United States Patent
Hostettler et al.

(12) 
(10) Patent No.: US 6,265,016 B1
(45) Date of Patent: Jul. 24, 2001

(54) PROCESS FOR THE PREPARATION OF SLIPPERY, TENACIOUSLY ADHERING, HYDROPHILIC POLYURETHANE HYDROGEL COATINGS, COATED POLYMER AND METAL SUBSTRATE MATERIALS, AND COATED MEDICAL DEVICES

(75) Inventors: Fritz Hostettler; David Rhum; Michael R. Forman; Michael N. Helmus; Ni Ding, all of New York, NY (US)

(73) Assignee: Schneider (USA) Inc., Plymouth, MN (US)

( * ) Notice: Subject to any disclaimer, the term of this patent is extended or adjusted under 35 U.S.C. 154(b) by 0 days.

(21) Appl. No.: 09/531,925

(22) Filed: Mar. 21, 2000

Related U.S. Application Data

(63) Continuation of application No. 09/126,374, filed on Aug. 27, 1998, now Pat. No. 6,040,058, and a division of application No. 08/382,478, filed on Feb. 1, 1995, now Pat. No. 6,017,577.

(51) Int. Cl.$^7$ ................................. B05D 3/02; B05D 5/00
(52) U.S. Cl. ...................... 427/2.11; 427/2.24; 427/2.28; 427/2.3
(58) Field of Search .................................. 427/2.1, 2.24, 427/2.25, 2.28, 2.29, 2.3, 536, 539, 340, 407.1, 409, 412.1

(56) References Cited

U.S. PATENT DOCUMENTS

| | | |
|---|---|---|
| 4,100,309 | 7/1978 | Micklus et al. ........................... 427/2 |
| 4,118,354 | 10/1978 | Harada et al. . |
| 4,119,094 | 10/1978 | Micklus et al. ........................ 128/132 |
| 4,373,009 | 2/1983 | Winn . |
| 4,459,317 | 7/1984 | Lambert . |
| 4,487,808 | 12/1984 | Lambert . |
| 4,613,517 | 9/1986 | Williams et al. .......................... 427/2 |
| 4,642,242 | 2/1987 | Solomon et al. ......................... 427/2 |
| 4,642,267 | 2/1987 | Creasy et al. . |
| 4,729,914 | 3/1988 | Klimet et al. ........................... 428/36 |
| 4,906,237 | 3/1990 | Johansson et al. . |
| 4,990,357 | 2/1991 | Karakelle et al. . |
| 5,026,607 | 6/1991 | Kiezulas . |
| 5,061,777 | 10/1991 | Yoda et al. ............................ 528/61 |
| 5,077,352 | 12/1991 | Elton . |
| 5,112,736 | 5/1992 | Caldwell et al. . |
| 5,132,108 | 7/1992 | Narayanan et al. . |
| 5,160,790 | 11/1992 | Elton ................................... 428/412 |
| 5,169,720 | 12/1992 | Braatz et al. ............................ 427/2 |
| 5,179,174 | 1/1993 | Elton . |
| 5,262,451 | 11/1993 | Winters et al. ....................... 523/112 |
| 5,290,585 | 3/1994 | Elton ...................................... 427/2 |
| 5,558,900 | 9/1996 | Fan et al. ............................ 427/2.28 |
| 5,576,072 | 11/1996 | Hostettler et al. .................... 427/532 |
| 5,662,960 | 9/1997 | Hostettler et al. ..................... 427/2.3 |
| 5,849,368 | 12/1998 | Hostettler et al. .................... 427/536 |
| 5,919,570 | 7/1999 | Hostettler et al. ................. 428/424.8 |
| 6,080,488 | 6/2000 | Hostettler et al. ................. 428/423.3 |
| 6,120,904 | 9/2000 | Hostettler et al. ................. 428/423.3 |

FOREIGN PATENT DOCUMENTS

| | | |
|---|---|---|
| 93 093 B2 | 12/1986 | (EP) . |
| WO 8909246 | 10/1989 | (WO) . |
| 90/01345 | 2/1990 | (WO) . |
| 92/11877 | 7/1992 | (WO) . |

*Primary Examiner*—Erma Cameron
(74) *Attorney, Agent, or Firm*—Vidas, Arrett & Steinkraus

(57) ABSTRACT

A process for the preparation of slippery, hydrophilic polyurethane hydrogel coating compositions, and materials composed of a polymeric plastic or rubber substrate or a metal substrate with a coating of a slippery, hydrophilic polyurethane hydrogel thereon, such that the coating composition tenaciously adheres to the substrate, are disclosed. The coating compositions and coated materials are non-toxic and biocompatible, and are ideally suited for use on medical devices, particularly, catheters, catheter balloons and stents. The coating compositions, coated materials and coated devices demonstrate low coefficients of friction in contact with body fluids, especially blood, as well as a high degree of wear permanence over prolonged use of the device. The hydrogel coating compositions are capable of being dried to facilitate storage of the devices to which they have been applied, and can be instantly reactivated for later use by exposure to water.

1 Claim, No Drawings

PROCESS FOR THE PREPARATION OF SLIPPERY, TENACIOUSLY ADHERING, HYDROPHILIC POLYURETHANE HYDROGEL COATINGS, COATED POLYMER AND METAL SUBSTRATE MATERIALS, AND COATED MEDICAL DEVICES

CROSS REFERENCE RELATED TO APPLICATION

This application is a Continuation of Ser. No. 09/126,374 filed Aug. 27, 1998, U.S. Pat. No. 6,040,058, which is a Division of Ser. No. 08/382,478 filed on Feb. 1, 1995, U.S. Pat. No. 6,017,577.

BACKGROUND OF THE INVENTION

This invention relates generally to the field of synthetic polymeric coating compositions for polymeric and metal substrates; and, more particularly, to hydrophilic hydrogel coating compositions which are slippery and which exhibit tenacious adherence to the substrate to which they are applied, and to medical devices bearing such hydrogel coatings thereon. Still more particularly, this invention relates to hydrophilic polyurethane hydrogel compositions. The hydrogel coating compositions and coated substrate materials are biocompatible and suitable for use on medical devices which come in contact with various body fluids.

In catheters and many other kinds of medical devices, it is often desirable to coat various plastic, rubber or metal parts thereof with products made from hydrophilic or certain other polymers that are slippery and which produce low coefficients of friction during use. However, one of the problems associated with the utility of such coatings is their inability to remain intact and abrasion-resistant during clinical use in body fluids such as blood. Catheters used in angioplasty, gastroenterology and other medical specialties, are commonly made of polymeric materials which most often are relatively hydrophobic and not inherently slippery or biocompatible. A surface modification is required in order to reduce the friction between the catheter and other devices with which they work, such as vascular sheaths, and also to reduce the friction between the vasculature or other anatomical passageways and the catheter itself. Almost all currently used catheters have some form of surface modification or coating applied to them. The ability of the coating to reduce frictional resistance, its durability, as well as its biocompatibility are the most important functional aspects of an effective surface.

Heretofore, catheters and other medical devices containing synthetic or natural polymers have often been coated with non-permanent compositions such as silicones and other slip agents, fluorocarbons, or hydrogels which, however, were usually not cohesively attached to the substrate surfaces. While such coatings can impart a low coefficient of friction to the surface of a medical device, they typically lack permanence with respect to frictional wear. Fluorocarbons, moreover, may peel or flake from the substrate, or when applied to a soft polymeric substrate material, may cause an increase in the stiffness of the material. In the case of marginally polar substrates used for the fabrication of catheters and other medical devices such as contact lenses, condoms, gastroenteric feed tubes, endotracheal tubes, and the like, a variety of polyurethane based compositions have been suggested as adhesive tie coats. For such uses the coating must exhibit wear permanence, low coefficient of friction in contact with body fluids, as well as extremely low toxicity and good biocompatibility. Whereas a number of polyurethane "tie coats" can improve adhesion to plastics and rubbers, they are oftentimes not compatible enough with respect to the polymer surface of the substrates to assure permanence of bonding for the intended medical application. In medical devices this can be a critical requirement for many clinical situations. Particular fields of medical specialties where such factors are important are enumerated below.

In Percutaneous Transluminal Coronary Angioplasty (PTCA) and Percutaneous Transluminal Angioplasty (PTA), the functional characteristics of balloon catheters include trackability through vasculature, crossability and recrossability of stenotic lesions, and retractability through the guiding catheter and the vascular sheath. These are dynamic functions that are fundamental to a successful and efficient interventional angioplasty procedure. They contribute to reduced trauma to the vasculature. In particular, recrossing of stenotic lesions is crucial to a successful outcome. High pressure angioplasty balloons, typically those made of polyethylene terephthalate (PET), can have problems with recrossability. This is because the relatively stiff PET material forms "wings" upon deflation after the first dilation. The winged profile of the deflated balloon can prevent recrossing of the stenotic lesion for a second dilatation. A durable slippery coating can aid in achieving recrossing of the lesion. Guiding catheters are better able to traverse tortuosity in the femoral artery and descending aorta with the help of a good slippery coating.

Stent catheters for use in vascular disease benefit from the characteristics imparted by a good slippery coating. Stent catheter delivery systems used in gastroenterology for opening of biliary passageways also benefit from a slippery coating with regard to traversing passageways leading to the site.

In coronary radiography, diagnostic catheters are used to deliver radiopaque fluid to the coronary arteries for visualization by x-ray fluoroscopy. These catheters benefit in the same way that guide catheters do from a good slippery coating, by aiding in traversing tortuosity in the femoral artery and the descending aorta.

U.S. Pat. No. 4,118,354 discloses the formation of polyurethane hydrogels which are reaction products of a polyisocyanate, having at least two isocyanate groups, and a polyether, produced from a plurality of alkylene oxides, 50 to 90% of which is ethylene oxide, added at random to a polyalcohol having at least two terminal hydroxyl groups, by the dispersal of the prepolymer reaction product into an aqueous liquid phase. Neither the formation of slippery hydrogel barrier coats upon plastic or metal substrates nor the affixation thereof to such substrates by means of covalent chemical bonds to assure durability of said coating upon exertion of dynamic forces thereon are described.

U.S. Pat. No. 4,373,009 describes a method for coating various polymeric substrates with polyurethane prepolymers containing free isocyanate groups and subjecting the thus coated substrates with a second coating of water-soluble copolymers of unsaturated monomers containing at least some isocyanate-reactive monomers as part of their backbone. It is postulated that the isocyanate treatment of the substrate results in firmly anchored tie coats even for polymers containing no isocyanate-reactive groups. No convincing evidence of covalent bonding of the urethane tie coat to the substrate is presented, nor is there any indication that the procedure is suitable for the use in critical medical devices where biocompatibility is a significant issue.

U.S. Pat. Nos. 4,459,317 and 4,487,808 discloses a process for treating a polymer substrate with a first coating of an isocyanate solution containing at least two unreacted isocyanate groups per molecule, and, optionally, a polymer; followed by a second coating of a high molecular weight polyethylene oxide, such that after curing of the isocyanate, the two coatings form a hydrophilic polyethylene oxide-polyurea interpolymer having a low coefficient of friction. Methods for applying a base coat of low molecular weight aromatic or aliphatic polyisocyanates dissolved in suitable organic solvents, followed by evaporating the solvent and then applying a second coat of a high molecular weight polyethyleneoxide polymer dissolved in an organic solvent are also disclosed. The second solution, which may also contain amine catalysts, is then evaporated and the two coatings are heated at elevated temperature in the presence of air which must contain enough moisture to react with the isocyanate of the first coating. The described processes are relatively time-consuming. The isocyanate coating is applied by spraying or dipping the substrate, and no evidence is presented that the isocyanate coating undergoes any reaction with the substrate surface to make it better adhering to the substrate surface. Medical devices made from a polymer substrate to which the coating has been applied, for use in body cavities, including especially the urethra, are also disclosed. Use of the coatings and coated medical devices in a blood medium, however, is not specifically disclosed, and it is believed that in the absence of bonding of the isocyanate coating to the substrate itself, the coatings and coated medical devices ultimately do not demonstrate the desired degree of permanence, especially in a blood environment.

U.S. Pat. No. 4,642,267 discloses a hydrophilic polymer blend which contains a thermoplastic polyurethane having no reactive isocyanate groups and a hydrophilic poly (N-vinyl lactam). The blend is said to be slippery in aqueous environments and is used as a low-friction coating for various substrates. Its use and performance in blood is not disclosed.

Published PCT Patent Application WO 89/09246 describes the use of shaped structures having polymer or metal substrate surfaces coated with crosslinked hydrophilic polymers, such as polyvinylpyrrolidone. The coated structures are said to be durable and exhibit a low coefficient of friction when wet. The use of polyethylene terephthalate (PET) substrates, which are often used in balloons for angioplasty catheters, is described. Crosslinking between the substrate and the coating is achieved by subjecting a hydrophilic polymer deposited on the substrate to thermally activated free radical initiators, UV light activated free radical initiation, or E-beam radiation. The adherence of the crosslinked hydrophilic polymer to the substrate surface is believed to be due to physical forces rather than to chemical bonding. A disadvantage of the process is that neither the thermally activated free radical initiators nor the UV initiators are biocompatible or suitable for medical uses. Furthermore, E-beam radiation applied to certain materials such as fluorocarbon polymers, which are often employed in medical devices, can be detrimental to these materials.

U.S. Pat. No. 4,990,357 describes coating compositions containing combinations of chain-extended hydrophilic thermoplastic polyetherurethane polymers with a variety of hydrophilic high molecular weight non-urethane polymers, such as polyvinylpyrrolidone. The coatings are made lubricious by contact with an aqueous liquid. The coatings adhere to a variety of polymeric substrates, including polyvinylchloride (PVC) and polyurethane (PU). A disadvantage of the coating compositions is that neither the thermoplastic polyurethane polymer, nor the hydrophilic non-urethane polymer can react with one another. Hence, it is not expected that these coatings give acceptable adhesion to most of the plastic substrates used in angioplasty devices.

U.S. Pat. No. 4,906,237 discloses the use of an osmolality-increasing compound such as glucose, sorbitol, sodium chloride, sodium citrate and sodium benzoate to improve the slipperiness and wetability of a surface coating for a polymeric substrate material which has first been coated with a non-reactive hydrophilic polymer. The coatings and coated substrates are said to be useful for situations where they come into contact with mucous membranes.

U.S. Pat. No. 5,026,607 describes the formation of a slippery coating of a urethane and a silicone or siloxane emulsion. A crosslinking agent, such as a polyfunctional aziridine, may be added to crosslink carboxyl functional groups in the coating with carboxyl functional groups on the substrate surface. The use of primers in the case of a PET substrate surface is also disclosed to effect better adhesion of the coating to the substrate. Alternative treatment methods to the use of primers, for example, the introduction of substrate surface functionality by means of plasma treatment or corona discharge to obtain hydroxyl, carboxyl, or amino functionality are also mentioned.

U.S. Pat. Nos. 5,077,352 and 5,179,174 describe the formation of lubricious coatings applied to a variety of substrates by means of forming crosslinked polyurethanes in the presence of polyethylene oxide polymers at high temperatures. No surface treatment of the substrate surfaces is described and the selection of the isocyanate compounds includes, in particular, reactive aromatic diisocyanates of the type not believed to be biocompatible. It is doubtful whether these methods can be recommended for use with intravenous catheter devices in view of the known carcinogenic nature of the amines which can result from the decomposition of such polyurethane polymers. Moreover, the high temperature polymerization procedures suggested can result in unacceptable physical changes of several of the polymeric materials utilized in angioplasty catheters.

Similar drawbacks pertain to the methods and compositions described in U.S. Pat. No. 5,160,790 describing the use of the same type of polyurethane polymers with various PVP polymers as the hydrophilic polymer species.

U.S. Pat. No. 5,132,108 discloses the use of plasma treatment of certain polymeric substrate surfaces, to introduce carboxyl and/or hydroxyl reactive groups thereon, utilizing an oxygen and water-containing plasma gas, followed by treating the resulting polymeric surface with a spacer component having amine groups. The treating step is conducted in the presence of a coupling agent, whereby covalent linkages are formed between the spacer component amine groups and the reactive sites of a modified hydrophilic polymeric substrate surface. Finally, an antithrombogenic, fibrinolytic or thrombolytic agent, such as heparin or other polysaccharides is contacted with the spacer component-treated modified polymeric surface. This method utilizes the introduction of relatively slow reacting carboxyl and/or hydroxyl groups onto the substrate surface, and encompasses too many processing steps for cost-effective production of medical devices. Although the resulting coated surfaces are biocompatible, they are not slippery and do not have low coefficients of friction.

U.S. Pat. No. 5,112,736 describes a method of introducing amino functionality on a variety of polymeric substrate surfaces, including polymers of polypropylene (PP), polyethylene (PE), polyvinylchloride (PVC), and polyvinylidenefluoride (PVDF), by plasma-treatment thereof in the presence of radiofrequency plasma discharge by means of ammonia, organic amine-containing gases, or mixtures of such plasma gases. The method is used for very hydrophobic hydrocarbon polymer articles such as PP membranes. It does not appear to give good results with PE polymers. PP films which contain amino groups on their surfaces are used for DNA sequencing on the membranes. No reference with respect to their use for attachment of hydrophilic PU polymers to highly hydrophobic substrates is made, nor does the reference disclose reliable methods to affix amino surface groups to PE surfaces which would be expected to work in the products and processes contemplated by the present invention.

The drastic influence of the chemical and physical composition of body fluids upon the permanence of low friction coatings when exposed to dynamic forces in such liquids has heretofore not been recognized. Whereas many slip additives, such as relatively low molecular weight silicones and a variety of hydrophilic polymers, exhibit slipperiness and relatively good permanence in the presence of water or saline solutions, they quickly lose their efficacy by exposure to dynamic forces in the presence of blood, a much more complex fluid composition.

Accordingly, there remains a need in the art of medical devices for an improved slippery coating material that demonstrates wear permanence, combined with the characteristics of biocompatibility, low toxicity and low coefficient of friction in contact with body fluids, especially blood.

SUMMARY OF THE INVENTION

The present invention encompasses cohesive, biocompatible, high water content, slippery polyurethane hydrogel coatings which are covalently bonded to and tenaciously adhere to plasma-treated polymeric plastic or rubber substrates, or chemically-treated metallic substrates, such as are utilizable for medical devices, which satisfy all of the above requirements. The present invention encompasses the tenaciously adhering coating compositions themselves, as well as materials composed of polymeric plastic, rubber or metal substrates coated with the coating compositions, and products fabricated from the coated materials, including, especially, coated medical devices such as catheters, catheter balloons and stents. The present invention also encompasses methods for applying such protective, wear-resistant, tenaciously adhering and biocompatible slippery barrier coatings to polymeric plastic or rubber substrates, and to metal substrates, particularly, to substrates for use in medical devices. The cohesively bonded, tenaciously adhering, slippery coating compositions and materials of the present invention are biocompatible, highly suited for use in contact with blood, demonstrate a low coefficient of friction with body fluids and a high degree of permanence when applied to a wide variety of medical devices in contact with various body fluids.

The method for applying the tenaciously adhering coatings of the present invention to polymeric plastic or rubber substrates, and to metal substrates, particularly for use in the fabrication of medical devices, generally consists of first plasma treating a polymeric plastic or rubber substrate or chemically-treating a metal substrate, to affix amine-containing groups, especially amino groups, onto its surface layers; next, applying a biocompatible intermediate hydrophilic polyurethane coating, containing isocyanate groups, which form covalent urea bonds by reaction of the terminal isocyanate groups of the coating intermediate with the previously formed amine-containing groups provided by the plasma treatment of the polymeric plastic or rubber substrate, or chemical treatment of a metal substrate, and which thereby become attached to the substrate, forming a "tie coat"; and, finally, converting the covalently bonded polyurethane tie coat into a hydrogel by exposure to and reaction with water or atmospheric moisture, thereby forming a protective, tenaciously adhering, hydrophilic, hydrogel coating on the intermediate tie coat to lubricate the outer surface of the device or part thereof which comes in contact with body fluids. The covalently attached protective polyurethane hydrogel coating is slippery when wet and the coated surface exhibits excellent permanence and wear characteristics when exposed to dynamic forces in the presence of various body fluids, especially blood. Furthermore, these coatings greatly enhance the biocompatibility of the resulting medical device during use. The hydrogel coatings also include compositions which contain additional hydrophilic polymers and other lubricious ingredients in addition to the hydrophilic polyurethane polymers.

It is known to those skilled in the art that surface treatment of polymeric surfaces by way of radio frequency plasma discharge conditions can activate the polymeric surfaces with respect to the physical and chemical characteristics of the boundary layers. It is further known that various surface coatings of medical devices can enhance the slipperiness and biocompatibility of the medical apparatus when in contact with body fluids. In order to obtain excellent adhesion, good strength, permanence, and biocompatibility of the barrier coats, their physical and chemical characteristics are immensely important. To affix barrier coats to various surfaces the use of polyurethane polymers and/or reactive isocyanate intermediates have often been suggested. It is well known that the isocyanate derivatives from aromatic polyisocyanates exhibit much greater reactivity or other interactions with substrate boundary layers, for example due to surface moisture or substrate polarity, than do the slower reacting aliphatic or cycloaliphatic isocyanates containing NCO groups that exhibit often not only appreciably lower rate of reaction, but also significant steric hindrance with regard to chemical interaction with active hydrogen compounds. The preferred isocyanate-derived hydrogels of the present invention are derived from aliphatic, cycloaliphatic, araliphatic, heterocyclic or aromatic polyisocyanates, most of which are known to yield urethane polymers possessing good biocompatibility and low toxicity. However, a predominant number of the latter polyisocyanates contain NCO groups which exhibit much lower order of activity than the aromatic isocyanates. Consequently, it is necessary to modify the chemical nature of the substrate surfaces in a manner to obtain practically immediate cohesive bonding of the boundary coatings to said polymer substrates.

To this end, it has been discovered that the affixation of amino groups to a polymer or rubber substrate can be accomplished by plasma treatment of the polymer or rubber substrate with a nitrogen-containing gas such as ammonia, organic amines, nitrous oxide (amino plus hydroxyl groups), nitrogen, and mixtures of these gases. In the case of very hydrophobic plastic substrates, for example, various grades of polyethylenes, nylons 11 and 12, and the like, we have discovered that optimal results are achieved by combinations of various oxidative chemical treatments or oxygen-containing plasma-treatments, to make the highly hydrophobic surfaces more polar or hydrophilic, followed by plasma exposure to nitrogen-containing plasma gases, or to gaseous ammonia or low-boiling amines, or mixtures thereof, to affix much more reactive amino groups onto the substrate surfaces. Although they are very hydrophobic, polypropylenes lend themselves more readily to plasma-treatment with nitrogen-containing gases because they contain a more labile hydrogen atom attached to a tertiary carbon in each repeating unit. Hence, suitable methods of amino group fixation are available for polyolefin polymers or other very hydrophobic plastic substrates. Amino groups can be affixed to a metal substrate by chemical treatment.

Amino groups can bring about instantaneous reaction of the substrate surface with any of the isocyanate derivatives contemplated in the invention. However, the amino groups are particularly useful with respect to improving reaction of the rather sluggish isocyanate species that are attached to secondary or tertiary carbon atoms of many polyisocyanates. After plasma exposure, or chemical treatment, of the polymeric or metallic substrate, respectively, a coating solution having between about 1% to about 20% solids, preferably between about 2% to 6% solids, of an isocyanate prepolymer containing free NCO groups, derived from water-soluble hydrophilic polyether polyols and one or more of aliphatic, cycloaliphatic, araliphatic, heterocyclic, and aromatic polyisocyanates, is applied to the treated substrate surface, allowed to dry, and the coatings are then converted to protective slippery, hydrophilic hydrogel layers upon the devices' surfaces by exposure to aqueous media or atmospheric moisture. If desired, the hydrogel formation can be catalyzed by procedures known in the art. Preferred polyisocyanates contemplated for use in the present invention include aliphatic, cycloaliphatic, araliphatic and aromatic isocyanates, especially diisocyanates, as well as their prepolymer derivatives.

In a preferred embodiment, the protective intermediate or tie coat is a hydrophilic polyurethane derived from a copolyether polyol of ethylene and propylene oxides, and isocyanates containing aliphatically bound NCO groups to optimize biocompatibility, since corresponding polyamines resulting from hydrolysis or biodegradation of such polyurethanes are in general biocompatible. Copolyethers facilitate handling of the prepolymer intermediates, since the preferred types are liquid at room temperature, thus presenting enhanced handling characteristics in commercial practice. The preferred plasma gases are ammonia or mixtures of ammonia with organic amines to optimize formation of amino groups on the substrate surface. The hydrogel formation which yields the desired polyurea hydrogel upon exposure to aqueous media can be conducted without a catalyst, or in the presence of catalysts such as inorganic bases, low-boiling tertiary amines, or water soluble primary or secondary polyamines that become part of the polyurea hydrogel polymer.

The coatings and the methods of the present invention are particularly well suited to affix tenaciously adhering, hydrophilic coatings to substrates such as polyethylene terephthalate, block copolymers of aliphatic polyethers and aromatic polyesters, block copolymers of aliphatic polyethers and polyamides, polyamides, polyimides, polyurethanes, hydrocarbon polymers such as polyethylene and polypropylene, synthetic hydrocarbon elastomers, and natural rubber. These polymeric substrates are the ones most often used in medical devices such as various types of catheters, and catheter devices for coronary angioplasty, including balloons.

The methods of the present invention for covalently attaching the hydrophillic polyurethane coatings to plasma- or chemically-treated surfaces are particularly useful for the manufacture of medical devices such as catheters, catheter balloons, and the like, which have coated surfaces that are vastly superior for use in blood, in comparison with the lubricious silicone coatings and/or other hydrophilic coatings previously commonly used. The wear performance upon dynamic exposure in blood is normally lost rather quickly by the coated medical devices of the prior art. In contrast thereto, the covalently bonded PU hydrogel coatings of the present invention, when affixed to various medical devices in accordance with the methods set forth In the present invention, exhibit exceptional durability even after many test cycles when exposed to dynamic forces in blood. These unanticipated observations and results represent a decided advance of the state of the art in the field of slippery coatings for medical devices.

The methods for producing the tenaciously adhering, slippery hydrophilic coatings of the present invention are based on the plasma treatment of various polymeric substrates with nitrogen-containing plasma gases to affix amino groups onto the substrate surface, or chemical treatment of metal substrates to affix reactive amino-siloxane groups onto the surface of those substrates, coating the resulting reactive surface with a hydrophilic polyurethane polymer coating solution, thereby instantaneously and covalently bonding the hydrophilic polymer permanently to the substrate, and then exposing the coated surface to water to form the desired final polyurea hydrogel coating. The polyurea hydrogel may additionally contain other lubricious polymers and/or slip additives, if desired. The coating is dried, packaged and sterilized before shipping the device to which it has been applied, and can be reactivated within one minute, or less, after immersion into aqueous fluids before clinical use. After reactivation the resulting hydrophilic polyurea hydrogel coatings exhibit excellent slipperiness, flexibility, toughness, outstanding permanence against premature wear in body fluids, and good biocompatibility. The covalently bonded slippery polyurethane-polyurea (PU/PUR) polymer hydrogels exhibit unusual endurance during the insertion of such medical devices in critical applications within body fluids having complex compositions. The coated devices are eminently beneficial for use in angioplasty devices, including balloon catheters, and exhibit remarkable slipperiness and unusual resistance towards manipulation in the presence of blood.

DETAILED DESCRIPTION OF THE INVENTION

The tenaciously adhering, hydrophilic coating compositions of the present invention are particularly suitable for medical devices, including catheters, balloons for use in conjunction with catheters, guidewires, metal tubing, and other devices having operational requirements and properties that can be improved by attaching slippery coatings to one or more surfaces of such devices which come in contact with body fluids. In accordance with the invention, the coatings include hydrophilic polyurethane polymers which are tenaciously adhered to the organic plastic or rubber polymer substrates or metal substrates from which the medical devices are fabricated by cohesive bonding, and upon exposure thereof to water, cause the resulting hydrogel coatings to form hydrophilic lubricating films on the apparatus or functional components thereof. The slippery coatings are characterized by good biocompatibility and good permanence of adhesion when exposed to dynamic forces in typical body fluids, such as blood and other chemically and physiologically complex fluid compositions.

The present invention also relates to a method for the production of coated medical devices by means of first exposing an uncoated polymeric device or precursor for subsequent fabrication into a device, or a parison for subsequent blow-molding into a balloon for use in conjunction with a medical device, to a high frequency plasma with microwaves, or alternatively to a high frequency plasma combined with magnetic field support, or chemically treating a metallic device, to yield the desired reactive surfaces bearing at least a substantial portion of reactant amino groups upon the substrate to be coated, which groups can combine instantly with the terminal isocyanate groups of the prepolymer intermediates deposited upon the reactively coated polymer or metal substrate surfaces. Particularly useful starting prepolymer intermediates for coating onto the polymer or metal substrate surfaces according to the present invention include hydrophilic polyurethane prepolymer intermediates derived from water-soluble polyether polyols and organic polyisocyanates. Preferred polyisocyanates include aliphatic, cycloaliphatic, araliphatic, heterocyclic, and aromatic polyisocyanates containing aliphatically attached terminal isocyanate groups. On account of the relatively slow reactivity of the isocyanate groups of this class, the plasma treatment of polymeric substrates or chemical treatment of metal substrates is conducted in a manner to yield rapidly reacting amino groups as the major desirable active species that is present on the boundary layer of the substrates. Therefore, the plasma treatment is carried out with plasma gases containing nitrogen atoms; and chemical treatment is carried out with amine group-containing compounds.

Quite surprisingly, the surface geometry of the polymeric materials used for the manufacture of medical apparatus remains relatively unaffected by plasma treatment. Furthermore, it has been established that if the plasma treatment parameters are followed carefully, the degree of amine-containing group, especially amino group, fixation on the surface is such that the isocyanate-containing coating intermediates which are deposited thereon do not crosslink prematurely before the hydrogel formation step is undertaken. These factors are of importance because it is believed that the slipperiness efficiency of the hydrogel is substantially improved by conducting the polymer formation reaction in such manner as to form hydrophilic polymer chains of substantial length and limited degree of crosslinking to optimize the mobility of the relatively elastic resultant molecular structure of the coating surfaces on which it is desired to achieve low coefficients of friction. Premature crosslinking or excessive crosslinking of the coatings surfaces is believed to be detrimental to achieving improved slipperiness due to maintaining a low coefficient of friction, lowering of dynamic drag forces, and preservation of high elasticity, which is known to improve frictional wear.

Typical polymeric substrates often employed for the medical devices of the present invention include thermoplastic polyurethanes (TPU), polyesters such as polyethylene terephthalate (PET), nylon polymers such as nylon-11 and nylon-12, block copolymers of polyether and polyester polymers (for example various HYTREL® block copolymers, available from DuPONT), block copolymers of polyether polymers and polyamides (for example, PEBAX® resin series, available from ATOCHEM), polyimides, polyolefins such as polyethylenes (PE) and polypropylenes (PP), synthetic rubbers thermoplastic hydrocarbon elastomers including SBR and EPDM (KRATON®, available from SHELL, and other similar commercial products from other sources), as well as natural rubber. For catheter applications used in angioplasty, components made from TPU, PET, nylons 11 and 12, HYTREL, PEBAX, and PE are preferred polymeric substrates. For catheter balloons used in coronary angioplasty preferred polymeric substrates are PET, nylons and PE.

It is often advantageous to pretreat the polymeric substrate surface before plasma treatment with polar or nonpolar organic solvents for a period of from about 15 seconds, or less, to longer than several minutes, in order to remove any surface impurities such as lubricants, antioxidants, plasticization agents, release agents, and the like. These impurities can originate from initial polymer manufacturing processes or from plastics forming techniques such as extrusion, injection-molding, blow-molding, and the like. Typical solvents which can be used for this purpose include alcohols such as methanol, ethanol, isopropanol, and the like; ketones such as acetone, methylethyl ketone, and the like; chlorinated hydrocarbons such as methylene chloride, 1,1,1-trichloroethane, and the like; hydrocarbons such as pentanes, n-hexane, petroleum ethers, other cleaning spirits, and the like; ethers such as diisopropyl ether, dioxane, tetrahydrofuran, and the like; and mixtures of the above. In the case of non-flammable cleaning solvents the removal of surface impurities can be carried out by means of vapor degreasers, a procedure well known in the art. It is also within the scope of the present invention to utilize aqueous solutions of nonionic, anionic, and cationic surfactants as washing fluids, if desired, followed by rinsing with water or distilled water to remove surface impurities that can interfere with the plasma treatment. Impurities on the substrate surface which are not part of the polymer matrix can detract from the formation of direct cohesive bonds with the substrates. Likewise, metal substrates should be degreased with organic solvents or washed with appropriate detergents or roughened mechanically, or treated with combinations of the above procedures, before application of organosilane, especially aminosilane, primers.

The speed of formation of cohesive bonds upon the substrate surfaces depends on the reactivity of the functional groups attached to a polymeric substrate surface by means of plasma treatment or to a metallic substrate surface by means of chemical treatment, as well as upon the rate of reaction of the terminal isocyanate groups that are present in the intermediate polymer coating affixed to the substrates. Fast reacting isocyanate groups that are attached directly to the aromatic ring structure can be made to form cohesive bonds with a variety of slower reacting functional groups that are present in the base plastic or rubber of a polymer substrate, on the plasma-treated surface of a polymer substrate, or on the chemically-treated surface of a metal substrate. Aromatic isocyanates and their derivatives can form cohesive bonds at from room temperature to 70° C., or higher, with reactive chemical functional groups such as hydroxyl, urethane, urea, amide, carboxyl, and carbonyl, that are either present in the original substrate polymer, or which have been affixed to a polymeric plastic or rubber substrate by oxidative- or plasma-treatment to yield, for example, hydroxyl or carboxyl groups; or which have been affixed to a metallic substrate surface by the chemical treatment thereof. Oftentimes non-plasma treated plastic surfaces having NCO-reactant functional components as part of their polymer make-up, or having oxidized surfaces, or even surface moisture, can result in reasonably good adhesion when exposed to aromatic polyisocyanates or derivatives therefrom. However, this procedure has been observed to give borderline results in the presence of most commercially available aliphatic, and in particular cycloaliphatic and sterically hindered araliphatic diisocyanates and their derivatives containing much slower reacting isocyanate groups.

Furthermore, from the standpoint of toxicity and/or biocompatibility, the use of polyurethanes derived from aromatic polyisocyanates and their hydrolytic or biodegradation aromatic polyamine by-products, is less desirable where the materials are in anatomical contact, because aromatic amines are potentially hazardous carcinogens. In this respect, caution must be exercised when the outer coatings on medical devices are employed in intravenous application in direct contact with body fluids, such as blood. Certain aromatic polyisocyanates have, however, been previously shown to be biocompatible. The use of aliphatic, cycloaliphatic, aralphatic, and heterocyclic polyisocyanates and prepolymers thereof containing only aliphatically-bound terminal NCO groups is, however, much preferred, because of the appreciably lower risk with respect to toxicity of their PU polymers, and in particular because of the known good biocompatibility of their polyamine degradation products.

Because of the considerably slower reactivity of the above mentioned aliphatically-bound, and oftentimes also sterically hindered isocyanate groups attached to the diisocyanates and derivatives thereof comprising the preferred embodiments of the present invention, it has been found advisable to plasma-treat the polymeric substrates used for the various medical devices encompassed by the present invention. Plasma treatment must be designed to affix primary and/or secondary amino groups preferentially or at least partially, upon the polymer surfaces of the substrate. These amino groups react instantly with the isocyanate groups of the prepolymer coatings intermediates, even before the coatings solvents are evaporated. Hence, the plasma treatment must be conducted in the presence of plasma gases that yield amino groups as at least a substantial portion of the functional groups affixed to the substrate surface. Plasma gases that can yield amino functionality must contain nitrogen as part of their chemical composition. Therefore, the plasma treatment is preferably carried out with plasma gases containing nitrogen atoms, such as ammonia, primary and secondary amines, nitrous oxide, nitrogen, other gases containing nitrogen moieties, and mixtures of such gaseous compounds. Ammonia and low molecular weight organic amines as well as mixtures thereof, being in the vapor state at relatively low temperatures, are preferred plasma gases. In the case of treatment of very hydrophobic substrate surfaces, for example, various polyethylene (PE) substrates, suitable conditions encompass first treating the substrate material with a plasma gas containing oxygen, either pure or in air or water vapor, or with a mixture of oxygen and one or more non-reducible gases, such as argon (Ar) and ammonia ($NH_3$), followed by a second treatment with either a nitrogen-containing plasma gas consisting of $NH_3$, low-boiling organic amines, or mixtures thereof, or simply an $NH_3$-containing or $NH_3$/low-boiling amine-containing gaseous post-stream soon after plasma treatment with a non-nitrogen-containing plasma. The net effect of such combination treatments is to affix a substantial portion of highly reactive amino groups into previously highly hydrophobic substrate surfaces and to simultaneously render them much more hydrophilic, which facilitates their interaction with the hydrophilic PU prepolymer to be affixed to the substrate as the "tie-coat".

The plasma treatment process of the present invention is applicable to treating a wide variety of organic polymeric substrate surfaces. Many of them have already been mentioned hereinabove, and they generally encompass thermoplastic materials, although it is within the scope of the present invention to utilize also thermosetting polymers as substrate materials for construction for some of the devices contemplated in the present invention. For example, it can be advantageous to crosslink catheter balloons to make them less susceptible to "winging" during deflation. As pointed out above, the substrate can be conditioned by means of washing or degreasing with solvents, or alternately by means of removing surface impurities with cationic, anionic, or nonionic surfactants followed by rinsing with water and drying. According to the present invention, the substrate is then exposed to a gaseous plasma containing nitrogen atoms. Preferred plasma gases include ammonia and/or organic amines, or mixtures thereof. Suitable organic amines are, by way of example, relatively low boiling primary and secondary amines having a structure (I–IV):

  I.,

  II.,

  III., and

  IV wherein $R_1$ and $R_2$ are monovalent hydrocarbon radicals having from 1 to about 8 carbon atoms, preferably from 1 to about 4 carbon atoms; $R_3$ is a divalent hydrocarbon radical having from 2 to about 8 carbon atoms, preferably from 2 to about 6 carbon atoms; and $R_4$ is hydrogen or a lower alkyl group.

Examples of suitable amines include methylamine, dimethylamine, ethylamine, diethylamine, methylethylamine, n-propylamine, allylamine, isopropylamine, n-butylamine, n-butylmethylamine, n-amylamine, n-hexylamine, 2-ethylhexylamine, ethylenediamine, 1,4-butanediamine, 1,6-hexanediamine, cyclohexylamine, N-methylcyclohexylamine, ethyleneimine, and the like.

Methods for plasma treatment with various plasma gases or combinations thereof are known in the art but generally lack the specificity demanded by the method employed in the present invention.

According to the present invention, for the case of ammonia and/or organic amines, or mixtures thereof as the plasma gases, a radio frequency (RF) of 13.56 MHZ, with a generating power of from about 0.1 Watts per square centimeter to about 0.5 Watts per square centimeter of surface area of the electrodes of the plasma apparatus is suitable. The plasma treatment comprises first evacuating the plasma reaction chamber to a desired base pressure of from about 10 to about 50 m Torr. After the chamber is stabilized to a desired working pressure, by flowing ammonia and/or organic amine gases, or mixtures thereof through the chamber at rates of from about 50 to about 730 standard ml per minute, preferably from about 200 to about 650 standard ml per minute, and a gas pressure of from about 0.01 to about 0.5 Torr, preferably from about 0.2 to about 0.4 Torr. A current at the desired allowed frequency and level of power is supplied by means of electrodes from a suitable external power source. Power output is from 0 to about 500 Watts, preferably from about 100 to about 400 Watts. The temperature of the plasma chamber is generally from about room temperature to about 50° C., and the treatment is usually carried out for a time of from about 30 seconds to about 10 minutes. The plasma chamber is initially at room temperature, however, during plasma treatment, the temperature in the chamber rises to a temperature not exceeding 60° C., due to molecular collisions. The plasma treatment can be performed by means of a continuous or batch process.

In the case of batch plasma treatment, the plasma surface treatment system known as PLASMA SCIENCE PS 0350 was utilized (HIMONT/PLASMA SCIENCE, Foster City, Calif.). The system is equipped with a reactor chamber, an RF solid-state generator operating at 13.56 MHZ capable of operating at from 0 to 500 watts power output, a microprocessor control system, and a complete vacuum pump package. The reaction chamber contains an unimpeded work volume of 16.75 inches in height, by 13.5 inches in width, by 17.5 inches in depth. For the application of the ammonia plasma, organic amine plasma, or a mixture of such plasma gases, the equipment is operated at a power output of from about 50 to about 400 Watts, a gas flow rate of from about 50 to about 730 standard ml/min for a time period of from about 15 seconds, up to about 10 minutes, under a vacuum, and at temperatures of from room temperature to about 50° C. A preferred range is from about 60 to about 120 Watts and an ammonia, organic amine or mixed gas flow rate of from about 700 to about 730 standard ml/min, a vacuum from 0.01 to 0.5 Torr, at a temperature of from about 30° C. to about 50° C., for a period of from about 15 seconds to about 3 minutes.

In order to define conditions for high permanence of adhesion of the hydrogel coatings, as well as the optimized degree of slipperiness and permanence in blood, a highly preferred method of operation consists of operating at a power range of from about 100 to about 400 Watts, an ammonia flow rate of about 200 to about 650 standard ml/min, a vacuum of from about 0.1 to 0.5 Torr, a treatment temperature of about 25° C. to about 40° C., and an exposure time of from about 30 seconds to about 3 minutes. Optimization procedures for the plasma treatment and the performance of the covalently bonded, tenaciously adhering, hydrophilic polyurethane hydrogel coatings can be determined on the basis of evaluation of dynamic drag forces versus exposure cycles and endurance in blood. Similar preferred conditions are utilized for nitrous oxide and nitrogen, or other gas mixtures containing nitrogen moieties as plasma gases.

Polymeric substrates which contain auxiliary chemicals such as antioxidants, ultraviolet and other light stabilizers, catalyst residues from their manufacture, organic and inorganic fillers such as calcium carbonates, clays, barium sulfate used as the radiopaque filler for medical devices, carbon blacks and other pigments, and the like, are also suitable as substrates for plasma treatment in accordance with the methods of the present invention.

The plasma treatment procedures of the present invention have been found to fade very slowly over a period of months. It is not certain whether this is associated with oxidative degradation of the functional groups attached to the substrate surfaces, or some other gradual decay processes. A preferred practice consists of coating the medical device within two months, or less, after the plasma treatment of the substrate material from which the device is fabricated has taken place. The highly preferred method consists of coating the plasma treated medical devices within two weeks, or less, after plasma treatment of the substrate material with the ammonia or organic amine plasma gases, or mixtures thereof.

Where the substrate to be coated is a metal, chemical treatment of the substrate surface with organosilane compounds having reactive aminoalkyl moieties that are attached to the silicone molecule to affix reactive aminosilane groups thereto must first be performed. Such aminosilanes hydrolyze rapidly in water and the resulting silanols can react and condense with reactive species of the metal surface to form quite stable cohesive anchor bonds therewith. The amino ends of the hydrolyzed and condensed aminosilane are available for reaction with functional groups, such as isocyanate groups of the prepolymer coating intermediate of the present invention. The aminosilane primer treatment of the metal surface, therefore, produces a similar effect as the plasma treatment of polymer substrates. Typical metal substrates, suitable for use in medical devices, which may be chemically treated include stainless steel and titanium, and metal alloys of steel, nickel, titanium, molybdenum, cobalt, and chromium, and other metals, such as the alloys, nitinol (nickel-titanium alloy), and vitallium (cobalt-chromium alloy). It is generally also recommended that the metal substrate surface be pre-treated by washing with a solvent to remove dirt and grease so that the silane groups may better attach themselves to the metal substrate surface. The amino and silane groups are connected by an intermediate hydrocarbon chain. The amino groups are outwardly terminal and are free to react with and covalently bond with free terminal isocyanate groups in the subsequently applied hydrophilic polyurethane pre-polymer intermediate coating. The length of the intervening hydrocarbon chain between the silane group and the amino groups can be tailored to the situation. Typically, the intermediate chain is a simple lower alkyl chain (i.e., ($-CH_2-$)x, where x is from 2 to 8).

Typical aminosilanes which are suitable for priming the metal surfaces of the devices contemplated by the present invention include, by way of example, g-aminopropyltriethoxysilane (A-1100; Union Carbide), an aqueous prehydrolyzed aminoalkyl silanol solution (A-1106 is a prehydrolyzed aminoalkylsilanol, prepared from aminosilane A-1100), γ-aminopropyltrimethoxy-silane (A-1110), β-aminoethyl-γ-aminopropyltrimethoxysilane (A-1120), and the like. Typical aqueous aminosilane priming compositions contain from about 0.5%, by weight, to about 3% by weight, of the aminosilane compound in water. After applying the hydrolyzed aminosilanes to the metal device by dip-coating or other means, water and alcohols from hydrolysis are removed by evaporation, and the primed surface is coated with a hydrophilic PU urethane adduct intermediate of the present invention to form the resulting covalently attached PU/UREA tie-layer on the metal surface. The tie-layer is then converted to the final hydrogel by the influence of moisture or aqueous medium.

According to the present invention isocyanate prepolymers which may be used for the preparation of the hydrophilic polyurethane coating intermediates comprise prepolymer reaction products of water-soluble mono- or polyfunctional polyethers, random copolyethers, and block copolyethers from 1,2-alkylene oxide and alternatively copolyethers from 1,2-alkylene oxides and tetrahydrofurane or tetrahydropyrane with organic polyisocyanates selected from the group consisting of aliphatic, cycloaliphatic, araliphatic, and heterocyclic polyisocyanates, and derivatives thereof. Preferred polyethers employed as starting materials for such isocyanate prepolymer adduct intermediates include water-soluble homopolyethers of ethylene oxide, copolyethers of ethylene and propylene oxides, copolyethers of ethylene and 1,2-butylene oxides, copolyethers from mixtures of all the above 1,2-alkylene oxides, and copolyethers of ethylene oxide and tetrahydrofurane. Highly preferred copolyethers are homopolyethers of ethylene oxide, and copolyethers from about 70% to about 85%, by weight, of ethylene oxide and from about 15% to about 30%, by weight, of propylene oxide. Copolyethers containing as much as from about 17.5% to about 30%, by weight, of propylene oxide are particularly preferred because they are liquid at room temperature, which greatly facilitates the handling of the resulting prepolymer adducts, and because they also remain liquid at temperatures appreciably below room temperature. The moderate levels of propylene oxide do not detract from the solubility of the resulting copolyethers in water, and the hydrophilicity of the final hydrogels makes them particularly suitable for the manufacture of lubricious wear-resistant hydrogel coatings.

Very surprisingly, it has also been found that monofunctional water-soluble polyether alcohols from ethylene oxide, as well as monofunctional copolyether alcohols from ethylene oxide and propylene oxide, containing a propylene oxide level of from about 15% to about 30%, by weight, are also well suited for the purpose of preparing isocyanate prepolymer intermediates for the preparation of lubricious hydrogels employed as top coats for medical devices. Furthermore, it has also been confirmed that admixtures of hydrogels comprising poly- and monofunctional polyether and/or copolyether isocyanate prepolymers as the base intermediates for hydrogel formation result in coatings exhibiting surprisingly superior lubricity and adhesive permanence when tested in body fluids, such as blood. Moreover, it has been discovered that the isocyanate prepolymers can be made in a single step by conducting the isocyanate prepolymer formation from mixtures of mono- and poly-functional polyethers. Furthermore, it is also feasible to conduct the prepolymer preparation by sequential addition of the monofunctional polyether to the isocyanate-terminated prepolymer from the polyfunctional polyether polyol. Consequently, the combinations consisting of prepolymers of water-soluble polyfunctional and monofunctional polyethers or copolyethers, and polyisocyanates selected from the group of aliphatic, cycloaliphatic, araliphatic, and aromatic diisocyanates, and derivatives thereof, are still other preferred embodiments of intermediate coatings of the present invention used for the manufacture of tenaciously adhering, hydrophilic hydrogel coatings.

Methods for the manufacture of such water-soluble polyfunctional homopolyethers, random copolyethers and block copolyether polyols, as well as monofunctional homopolyether and copolyether alcohols, are well known in the art. Typically, monofunctional polyether alcohols and polyfunctional polyether polyols are derived by the addition of 1,2-alkylene oxides to monohydric or dihydric alcohols or phenols, or polyhydric alcohols or phenols in the presence of alkaline catalysts. Copolyether diols from ethylene oxide and tetrahydrofurane or larger ring cyclic oxides are generally made in the presence of Lewis acids as the catalysts, as is well known in the art. Representative monofunctional and polyfunctional starters for the 1,2-alkoxylation reactions are, by way of example, methanol, ethanol, isopropanol, butanol, amyl alcohols, hexanol, 2-ethylhexanol, lauryl alcohols and other fatty alcohols, phenol, cresols, higher alkyl phenols, naphthols, and the like; water, ethylene glycol, diethylene glycol, propylene glycol, dipropylene glycol, 1,4-butanediol, 1,6-hexanediol, neopentylene glycol, resorcinol, hydroquinone, bisphenol A, xylenols, glycerol, trimethylolpropane, pentaerythrtol, a -methyl glucoside, sorbitol, sucrose and the like. Lower carbon monofunctional alcohols are generally preferred starters for monofunctional polyethers and copolyethers. Water and lower carbon aliphatic glycols are preferred for difunctional polyether and copolyether diols. Glycerol and trimethylpropane are highly preferred for the manufacture of trifunctional polyether and copolyether polyol intermediates.

The monofunctional and polyfunctional hydroxyl-terminated polyethers and copolyethers, especially polyether and copolyether alcohols and polyols, used as starting materials for the manufacture of hydrophilic isocyanate prepolymers of the present invention have equivalent weights (EW) per hydroxyl in the range of from less than about 500, to greater than about 20,000. Within this general range, preferred EW's for monofunctional polyether alcohols and copolyether alcohols are from about 2,000 to about 10,000, and highly preferred values range from about 3,500 to about 6,000. Further within the above broad ranges, preferred EW ranges for the glycerol and trimethylolpropane 1,2-alkylene oxide adducts are from less than about 1,500, to greater than about 7,500, while the most preferred EW ranges for these trifunctional products are from about 1,500 to about 2,500. With respect to difunctional polyether diol and copolyether diol adducts, preferred EW values range from about 750 to about 5,000, and a highly preferred range is from about 1,000 to about 4,000. The EW values of these polyether alcohols and polyols can be determined by phthalation or acetylation of the hydroxyl group by well known analytical techniques such as, for example, ASTM Method D-4274-88.

As is well known, the above-described polyether adducts from 1,2-alkylene oxides are normally prepared by means of base catalyzed oxide addition to mono- and polyhydric alcohols or phenols. Typical oxyalkylation catalysts are hydroxides and alkoxides of alkaline earth metals such as sodium and particularly potassium. Representative of such catalysts are potassium and sodium hydroxide for the manufacture of polyfunctional polyethers, and sodium and potassium alkoxides of lower monohydric alcohols and phenols such as the methoxides, ethoxides, phenoxides, and the like, when the desired polyethers are intended to be monofunctional. Such catalysts are generally used at levels of from about 0.05% to greater than about 0.3%, by weight, based upon the oxide adducts being made. However, catalyst residues must be removed prior to the reactions with polyisocyanates, because they will catalyze unattractive side reactions of isocyanates, such as trimerization and dimerization of isocyanates, or formation of allophantes from urethanes formed during the prepolymer step, formation of urea and biuret derivatives, or additional undesirable byproducts. Consequently, they must be removed by way of ion exchange reactions or other means after the oxyalkylation step. Similarly, if the polymerization is performed with acidic catalysts such as Lewis acids, they must also be removed by known methods, because they will slow down the reaction of the isocyanate group with hydroxyl-terminated polyethers. The presence of undesired alkali metals can also be examined by well established analytical procedures (ASTM D-4668-87). In this regard, the total presence of sodium and potassium metals in the polyethers should be within the range of from 0 to 10 ppm, preferably less than about 5 ppm, to avoid complications during the prepolymer reaction step.

Furthermore, it is important that the hydroxyl-containing hydrophilic polyethers contain very low levels of water prior to their reaction with polyisocyanates to form the corresponding prepolymers. Moisture can lead to urea group formation and subsequent gelation of such prepolymers by means of biuret crosslinking reactions which interferes with the subsequent coatings steps. Consequently, it is advisable to dry such polyethers by means of azeotropic distillation with aromatic hydrocarbons such as toluene or xylenes, by careful drying under vacuum at 100 to 120° C. at pressures of from less than about 5 to about 10 torr, or by combinations of azeotropic distillation and vacuum drying. These procedures are well known in the art.

After removal of catalysts, the resulting polyether alcohols or polyether polyols must be protected from oxidation in the presence of air by means of antioxidants. Most of the antioxidants used in commercial practice are not biocompatible and are not useful for applications involving medical devices of the type employed for clinical use in body fluids. On account of the relatively short insertion times of the medical devices of the present invention, certain antioxidants such as IRGANOX 1010, IRGANOX 1076 (CIBA-GEIGY), SANTONOX R (MONSANTO), and similar compounds can be considered to be acceptable for short use in the bloodstream, since they have exhibited a low order of toxicity in other applications. The antioxidant level is generally at from about 0.01% to about 0.05%, by weight, based on the hydroxyl-terminated polyether intermediate.

Suitable polyisocyanates for the manufacture of the hydrophilic polyether and copolyether prepolymer intermediates of the present invention include aliphatic, cycloaliphatic, araliphatic, heterocyclic and aromatic polyisocyanates of the type described by W. Siefken in Annalen der Chemie, Volume 362, pages 75–136, and in many other publications well known in the art. Preferred polyisocyanates include the commercially available diisocyanates such as 1,4-tetramethylene diisocyanate, 1,6-hexamethylene diisocyanate (HDI), trifunctional biuret and isocyanurate derivatives of HDI (MILES CORPORATION, Polymers Division; OLIN CORPORATION, Olin Chemicals), isophorone diisocyanate (IPDI), the isomer mixtures of methylene bis(4-cyclohexylene diisocyanates) known as DESMODUR W(® (MILES CORPORATION, Polymer Division), m-xylylene diisocyanate, p-xylylene diisocyanate, m-tetramethylxylylene diisocyanate known as TMXDI-meta® (CYTEC INDUSTRIES, Inc., Stamford, Conn.), p-tetramethylxylylene diisocyanate, the isomer mixture of bis(isocyanatomethyl)1,3-cyclohexylene (MITSUBISHI GAS CHEMICAL CO., Inc., Toyko, Japan), and trans 1,4-cyclohexylene diisocyanate. A number of the above-described di- and poly-isocyanates are commercially available. Most of them are known to yield biocompatible polyurethane polymers, since they are known to yield amine hydrolysis products which are known to exhibit very low toxicity. This has been demonstrated in the case of HDI, IPDI, DESMODUR W®, and is expected to be valid for TMXDI and other commercially available diisocyanates. Preferred polyisocyanates for the purpose of the present invention include aliphatic, cycloaliphatic, araliphatic and aromatic isocyanates. Particularly preferred polyisocyanates include 1,6-hexamethylene diisocyanate, and especially its trifunctional isocyanurate and biuret derivatives, all of which exhibit low toxicity, isophorone diisocyanate and its trifunctional isocyanurate derivatives, DESMODUR W®, and TMXDI-meta®.

For the purpose of the present invention, the polyether and copolyether prepolymer adducts prepared from the above described polyethers are preferably reacted with about two equivalents of the isocyanate component per equivalent of the polyether hydroxyl compound to react most, if not all, of the hydroxyl groups which are available for conversion to the corresponding urethane polymer. In addition, it is also feasible to utilize the above diisocyanates as chain-extension agents to increase the chain length of difunctional prepolymers derived from polyether diols or copolyether diols. In this case, the relative ratio of the reactants is adjusted accordingly to compensate for the chain lengthening action. In most cases the aliphatically attached isocyanate groups are either sterically hindered, attached to secondary carbon atoms (═CH—NCO) or tertiary carbon atoms [—C(CH$_3$)$_2$—NCO], for example, such as in TMXDI, all of them contributing sufficiently to slow down the prepolymer formation sufficiently as to necessitate the use of isocyanate catalysts for the formation of the prepolymers. With a few somewhat faster reacting polyisocyanates, such as for example, HDI and its derivatives, other straight-chain, non-hindered alkylene desiccants, or m- and p-xylylene diisocyanates, the prepolymer adduct reaction can be conducted without a catalyst, if desired. However, even with these materials the catalytic prepolymer process is usually more cost effective.

With the possible exception of m- and p- TMXDI which are only moderately toxic as the free diisocyanate, in all other cases it is prudent to conduct the prepolymer formation is such manner as to minimize the presence of unreacted free diisocyanate. This is feasible by judicious selection of the NCO/OH reactant ratios and/or selection of the appropriate catalysts and catalyst levels during the formation of the prepolymers. Furthermore, it is also feasible to remove unreacted free diisocyanates by means of thin-film evaporators, a procedure well known in this art. In the case of the highly hindered and slow reacting diisocyanates the use of the catalysts is definitely recommended and is, in fact, often essential to react substantially all the hydroxyl groups of the starting polyethers polyol intermediates.

The isocyanate reaction for the formation of prepolymers from hydroxyl-containing polyethers can be catalyzed by means of tertiary amines, or many metal catalysts, as is well known in the art. Although tertiary amines are very desirable catalysts for the formation of the PU/PUR hydrogel polymers and copolymers from the PU prepolymers of the present invention, they are not particularly useful for the manufacture of the NCO-terminated PU prepolymers because they can accelerate undesirable side reactions, for example, trimerization of free NCO groups which can lead to premature gelation of such prepolymers. The selection of appropriate metal catalysts is also difficult because many of them can also cause trimerization, or are too toxic for use in the medical devices of the present invention. On account of their high catalyst activity, high selectivity with respect to the hydroxyl reaction, and favorable cytotoxicity when used at low concentrations, tin compounds are highly preferred catalysts. Tin catalysts, such as stannous acylates, and dialkyltin compounds, such as dialkyltin diacylates and dialkyltin oxides, are known to be highly effective in very small concentrations. Because they are not known to catalyze trimerization reactions of isocyanates and they are powerful catalysts for the hydroxyl-isocyanate reaction, they are expected to be satisfactory for the intended uses of the devices contemplated by the present invention. In this respect commercially available compounds such as stannous octoate, stannous oleate, dibutyltin dilaurate, dimethyltin dilaurate, dioctyltin oxide, and other similar tin compounds are known to be biocompatible when used in moderate amounts. Furthermore, catalyst levels should be kept as low as possible to avoid any side reactions. Typical catalyst concentrations for tin compounds are from 5 to about 300 parts per million (ppm), preferably from about 10 to about 50 ppm, and most preferably, from about 10 to about 20 ppm. In the case of HDI and its derivatives the rates of reaction are sufficiently high to avoid the use of catalysts for the prepolymer formation altogether, if desired. Moreover, it is highly advisable to remove unreacted HDI by means of thin-film evaporation to avoid toxic work environments. Reaction times when using catalysts are from about 2 hours to not more than about 6 hours.

Reaction temperatures for the prepolymer formation can vary from room temperature up to as high as about 85° C. to 90° C., with a preferred reaction temperature being from about 50° C. to 70° C. For the purpose of achieving good shelf stability of the prepolymer intermediates, the use of the lowest practical catalyst level is generally preferable. It is often possible to have satisfactory shelf lives for such prepolymers of from about 4 to about 6 months, or more, when they are stored near room temperature or somewhat below. Recent publications with respect to the catalysis of isocyanates of interest for the purpose of the present invention have been published in Modem Paint and Coatings, June, 1987 (E. P. Schiller and J. Rosthauser, MOBAY CORP.), and by K. Hatada et al., Journal of Polymer Science: Part A: Polymer Chemistry, Vol. 28, 3019–3027 (1990) [Reactions of isophorone diisocyanate with amine and tin catalysts].

The progress of the isocyanate reaction can be followed by measuring the disappearance of the hydroxyl groups by means of infrared techniques, or more accurately, by analysis for NCO content (ASTM D-4666-87). The reaction can be discontinued when substantially all hydroxyls have reacted, or when the expected calculated % NCO content, or a level near that value has been attained. The reaction duration depends upon the catalyst type and concentration, the nature of the ingredients and the reaction temperature, and can be defined quite precisely for particular combinations of reactants. In any event, even at very low metal catalyst levels, it is feasible to achieve conditions that can complete the reactions within from as low as 3 to about 12 hours, at temperatures ranging from about 50° C. to about 80° C. A preferred reaction temperature range is from about 50° C. to about 70° C. If HDI is utilized without a catalyst, similar reaction parameters apply.

It is within the scope of the present invention to conduct the prepolymer formation in the presence of suitable solvents to facilitate handling of process ingredients, moderate the exothermic reaction processes, as well as to obtain solutions of the prepolymers before making up the final coating compositions that involve the same or other solvents than the ones utilized in the reaction step. The use of moderate amounts of solvents during prepolymer formation is a preferred operating procedure because the resulting intermediates exhibit lower viscosities and better handling and storage characteristics. For the purpose of achieving suitable reaction conditions during the prepolymer formation step, the total solids content of the reactants utilized in the prepolymer synthesis can vary over a wide range, for example from about 20%, by weight, to as high as about 80%, by weight. A preferred range is from about 30%, by weight, to about 70%, by weight, and a most preferred range is from about 40%, by weight, to about 60%, by weight. The solvents which are utilized in the prepolymer process should be free of water ("urethane-grade" solvents), and non-reactive with the isocyanates used in the process. Such solvents or often commercially available or can be dried suitably by means of molecular sieves, a procedure well known in the polyurethane art.

The solvents should preferably have a boiling point above the reaction temperature utilized for the prepolymer formation, but should boil low enough to allow convenient evaporation of the diluents after the subsequent coating operation of the plasma-treated substrate material of the medical device or other object. Furthermore, the solvents should not be detrimental to the materials of construction used as the substrate material of the medical devices during the subsequent coating operations. Typical solvents which are useful for the preparation of the isocyanate prepolymers of the present invention include those in which both the polyisocyanates as well as the hydrophilic polyethers are soluble, to afford homogenous reaction. Aromatic hydrocarbon solvents such as benzene, toluene, xylenes, and the like, ketones such as methylethyl ketone, ethers such as methyl tert, butyl ether, tetrahydrofurane, dioxane, esters such as methylethoxy acetate, methylisopropoxy acetate, ethyl acetate, butyl acetate, ethyl formate, chloroalkanes such as 1,1,1-trichloroethane, and mixtures of these solvents, are among the media useful for the preparation of the hydrophilic prepolymers of the present invention. Solvents which can be admixed after the prepolymer formation to make up the final coating solution can also include lower boiling solvents such as pentanes, hexanes, methylene dichloride, acetone, and other low boiling solvents that can speed up the process of evaporation after coating of the plasma-treated substrate material.

In accordance with the present invention the initial coating step of the plasma-treated substrate with the solution of the original prepolymer intermediate can be performed at a solids content of from about 1%, by weight, to about 20%, by weight, or higher, based upon the total weight of the prepolymer and the solvent. A preferred solids content is from about 1.5%, by weight, to about 8%, by weight, and a most preferred coating solution has a solids content of from about 1.5%, by weight, to about 4%, by weight, based upon the coating composition. The coating process can be performed by means of dip-coating, continuous coating by mechanically pushing or pulling the device through a coating trough, or alternatively by means of spray coating. The amount of coating solution to be deposited upon the device is determined by means of the various process parameters including the measurement of lubricity and durability of the finished hydrogel coating deposited upon the functional device. In the case of dip coating or traverse coating through a trough, the coating contact time can vary from a few seconds to as long as 1 minute, or more. The efficacy of the coatings depth, even at thicknesses of from less than about 1 mil about to 3 mils, has been found to be sufficient to achieve the desired objectives of excellent lubricity and permanence. In the event that the coating thickness becomes excessive, for example at from greater than about 5 mils, there exist the dangers of limiting the wear properties of the coated medical device and of causing the flaking off of portions of the coating.

In accordance with the present invention the lubricious polyurethane hydrogel surface coating deposited upon the plasma-treated substrate is generally formed by means of two consecutive steps. The first step involves applying the prepolymer coating intermediate, dissolved in one or more suitable solvents described above, and then allowing the solvents to evaporate. During this coating step, at least some of the free NCO groups present in the prepolymer coating solution react instantaneously with amino groups which are affixed to the substrate surface and form covalent cohesive urea (UR) bonds with the modified reactive "tie-coat" surface. This occurs even before the solvents have begun to evaporate. After removal of all, or almost all of the solvent, the next step includes exposing the remaining free NCO groups of the hydrophilic prepolymer intermediate to atmospheric moisture or to water by such means as dip coating or other techniques to form the final tenaciously adhering, hydrophilic, slippery polyurethane-polyurea (PU/PUR) hydrogel coatings.

One essential feature in all of the embodiments of the present invention is the use of a base "tie-coat", deposited onto a plasma- or chemically-treated substrate, and having at least a substantial portion of functional surface groups in the form of amino groups capable of reacting essentially instantly with the relatively slow reacting isocyanate endgroups of the hydrophilic polyurethane prepolymers of water-soluble polyethers and aliphatic, cycloaliphatic, araliphatic, or heterocyclic polyisocyanates or derivatives thereof, which become the covalently bonded cohesive hydrophilic polyurethane-urea (PU/UR) "tie-coats" attached to the substrate. These "tie-coats" can be converted to the desired polyurethane-polyurea (PU/PUR) hydrogels by the influence of aqueous media, or a mixed or double-coated blend thereof comprising additional hydrophilic PU hydrogel prepolymers having the original or different compositions can also be treated with water to copolymerize the PU/UR "tie-coats" with the additional PU prepolymers to form the final lubricious polyurethane-polyurea (PU/PUR) hydrogel copolymer coating compositions.

The covalently bonded PU/PUR hydrogel coating or covalently bonded copolymer PU/PUR hydrogel coating of the present invention has a water content of at least 70% of the weight of the hydrogel coating(s), and preferably a water content of from about 85% to about 90%, by weight, of the hydrogel coating(s). Such PU/PUR hydrogel polymer or copolymer PU/PUR hydrogel coatings can contain water in excess of 95%, by weight, based upon the dry hydrophilic hydrogel polymer(s) and yet maintain properties of uniformity, elasticity and stability. The PU/PUR hydrogel coatings or PU/PUR copolymer hydrogel coatings are extremely stable over time, however, for practical purposes, it is more convenient to convert the hydrogel to a dry, reactivateable form so that medical devices which have been coated with the lubricous coatings according to the present invention can be easily packaged using conventional dry, sterile packaging techniques. The resulting dry, reactivateable outer hydrogel coat is instantly reactivateable at the time of use of the device by immersing the device in an aqueous medium.

The final step of hydrogel formation can be conducted in the absence of a catalyst, or also in the presence of a suitable catalyst, if desired, to accelerate the reaction of water in liquid or vapor form with the free isocyanate remaining after the first coatings sequence, or double-coating sequence of the various NCO-reactive prepolymer intermediates. The ensuing water reaction forms interconnecting urea groups to form the long hydrogel polymer chains whose exact polymer macro- and micro-domains determine the lubricity and permanence of the resulting coatings. It is further feasible to conduct the hydrogel formation in the presence of instantly reacting water-soluble aliphatic, cycloaliphatic, araliphatic, heterocyclic, or still other diamines, to form the chain-extended hydrogels. Inorganic diamine derivatives such as hydrazine or substituted hydrazines containing active hydrogens on the nitrogen atoms are suitable chain-extenders. Such diamines are usually dissolved in the aqueous phase, followed by dip coating, spraying, or similar techniques to rapidly convert the coating to the desired hydrogel.

As pointed out above, the second step of the coatings method comprises transformation of the initially formed and partially covalently bonded hydrophilic PU/UR isocyanate prepolymer intermediate that was deposited onto the substrate during the first step, into the final polyurethane hydrogel polymer by the action of water, either in the form of an aqueous coatings solution by means of dipping, spraying, and other methods, or by exposing the coated substrate to atmospheric moisture. Other process options and embodiments have also been described above. The hydrogel formation can be conducted in the absence of a catalyst, in the presence of a catalyst, or also in the presence of an amine chain extender that can function as a reactive ingredient for rapid lengthening of the polymer chains and simultaneously as a catalyst to speed up the hydrogel formation. It is also feasible to perform the hydrogel synthesis in the presence of both, a catalyst and an amine chain extender, or also with an amine chain extender alone in the absence of another catalyst. A still further alternative consists of performing the hydrogel formation by means of compounds containing a catalytic moiety, as well as an isocyanate reactant group such as, for example, N,N-dimethylalkanolamines, amines which contain both, tertiary amine groups as well as reacting primary or secondary amine groups. It is also within the scope of the present invention to utilize mixtures of the above identified catalysts and any of the reactant catalyst species.

Preferred catalyst for the formation of the hydrogel polymers comprise low boiling tertiary amines such as trimethylamine, triethylamine, diethylmethylamine, tripropylamine, triisopropylamine, or other low-boiling amines that can be removed readily by drying of the finished hydrogel coating. The low-boiling tertiary amine catalysts can be employed as aqueous solutions wherein the medical devices are submerged after the coating operation, or they can be admixed in suitable concentration with a moist stream of air that contacts the hydrophilic prepolymer coating after evaporation of the coating solvent. The highly preferred catalyst/chain extender is ethylenediamine, which is best dissolved in water for dip-coating the medical device therein. Typical catalyst concentrations of the amine catalysts in water are from as low as 0.03%, by weight, to as much as 0.3%, by weight, or higher. Preferred levels for ethylenediamine are in the range of from 0.05%, by weight, to about 0.15%, by weight. In the case of hydrogel formation by means of moist vapors contacting the prepolymer coated substrate, the catalyst concentrations are held near the lower levels to provide safer handling characteristics. It is also feasible to recirculate catalyst-containing moisture streams to sidestep excessive catalyst removal and/or recovery problems. With this catalyst technique it is generally feasible to reduce cure times for hydrogel formation to about 6 to 8 hours, or in most instances even considerably less. The hydrogel formation is also accelerated by increasing the exposure temperature above room temperature, for example from about 25° C., to as high as about 70° C.

However, it is also within the scope of the present invention to utilize higher boiling tertiary amines that can be applied as aqueous solutions to accelerate the water/isocyanate reaction by means of the typical amine catalysts well appreciated by those skilled in the polyurethane art. The disadvantage of utilizing high boiling amines, which are often toxic or irritants, is the requirement to remove them from the cured hydrogel by time-consuming methods such as rinsing with water.

In the case of non-catalyzed processing, the coated devices are exposed to atmospheric moisture, preferably at 50% relative humidity, or higher, for a period of from 6 hours, or longer, at temperatures ranging from room temperature to as high as 80° C. At the higher temperature ranges cure time is about 6 hours, or longer, while at room temperature and relatively low humidity cure times of as long as from about 24 hours to about 72 hours are often required to obtain consistent results.

In the absence of basic catalysts the hydrogel formation normally takes from 24 to 48 hours, or more, to attain reliable cure rates with slow reacting NCO end groups. Besides organic amine catalysts and/or amine chain extenders, it is also feasible to conduct the hydrogel formation in the presence of moderately basic inorganic salts which can be removed from the cured hydrogel by means of adequate flushing with water. However, this procedure can be more expensive on account of more complex processing. Nevertheless, typical aqueous solutions containing inorganic salts that are suitable to cure such hydrogels include, among others, sodium carbonate, sodium bicarbonate, sodium borate, sodium acetate, as well as other alkali salts of weak acids, and the like. Aqueous salt concentrations of from 0.05%, by weight, to about 0.2%, by weight, are generally sufficient to speed up the formation of the hydrogel. However, rinsing of the coated devices with fresh water can take up to 24 hours to reduce the salt content in the hydrogel sufficiently to make it safe for use under clinical conditions. Consequently, the use of catalysts which can be removed by way of simple evaporation, or by essentially quantitative reaction with the isocyanate prepolymers is preferable.

An alternate method for curing of the coated prepolymer intermediate to form the hydrogel consists of submersion of the coated device in water having a temperature of from about room temperature to about 80° C. for a period of from about 30 seconds to as long as about 30 minutes, depending upon the temperature of the aqueous bath. The higher the water temperature, the lower the required dip time. This process is accelerated by the presence of water-soluble tertiary amines, some of which are illustrated above. Still another method which has been found suitable for accelerating the cure of the hydrogels of the present invention involves the use of di- or higher functional reactive polyamines which act as catalysts and reactants for the formation of the corresponding polyurea hydrogels. Typical diamines which can be dissolved in water include ethylenediamine, 1,4-butanediamine, 1,6-hexanediamine, piperazine, dimethyl piperazines, and others. Ethylenediamine is generally preferred and has given very good results. These amines have the further advantages of being able to function rapidly at room temperature, and they are also capable of forming interpenetrating networks with other lubricious polymers.

After formation of the tenaciously adhering, hydrophilic, slippery hydrogel polymer it is essential to be able to handle the medical apparatus for the purpose of packaging, sterilizing, shipping, and the like. For that purpose it is desirable to dehydrate the hydrogel and transform it to a substantially dry state. This drying step is best accomplished by means of vacuum evaporation of the wet hydrogel. At the same time, if the hydrogel has been manufactured in the presence of low boiling amine catalysts it serves the useful purpose to remove any remaining amounts thereof to make the device safe with respect to irritant chemicals for later clinical applications. The vacuum drying step can be performed at temperatures of from room temperature, about 23.5° C., to as high as about 60° C. under a vacuum of from about 5 Torr, or lower, to as high as about 200 Torr, or higher, for sufficient time periods to remove substantially all moisture and/or volatile contaminants.

After evaporation of moisture and any other undesired process chemicals, if any, the coated medical device is packaged in moisture-proof packaging, for example, in properly sealed polyethylene films suitable for this purpose. Thereafter, the device is sterilized by conventional means well known in the pharmaceutical industry. The hydrogel coatings of the present invention are sterilized by means of γ-radiation without compromising the performance of the hydrophilic hydrogel coating with respect to wear properties upon exposure to mechanical forces in blood. It is also believed that such coatings are not adversely affected by means of the well-known ethylene oxide sterilization procedure.

The dry and rather elastic hydrogel coatings of the present invention rehydrate rapidly to the hydrogel upon immersion into water or saline solution. The slipperiness as well as dynamic wear performance characteristics of a medical device in blood are restored and substantially unchanged after going through the transition phases. After immersion into distilled water or saline (Ringer's) solution rehydration is observed to take place quickly, within from less than 10 seconds to no longer than about one minute, depending upon exact procedural conditions.

As mentioned above, a further important embodiment of the present invention involves the formation of dry hydrogel coatings by the removal of water, sterilization by means of γ-rays, and activation by exposure to saline solution or water just before clinical use of the device. The most cost-effective manufacturing process of the present invention involves applying a first coating of the cycloaliphatic prepolymers in an organic solvent to the device, letting it dry, and dip-coating the dried device into an aqueous solution containing a reactive diamine chain extender. After hydrogel formation, the hydrogel coating is then dried, sterilized, and reactivated at the time of clinical use.

The following examples are further illustrative of various aspects of the present invention. They are not deemed to be limiting in any way. The scope of the present invention is set forth by the set of claims appended hereto. Other embodiments of the various aspects of the invention within the scope of the claims will be evident to those skilled in the art. The examples describe all of the several parameters involved in plasma-treating the substrate polymers, preparing the hydrophilic isocyanate prepolymers of the present invention, affixing them covalently to the treated substrates, and finally converting the attached hydrophilic top coats to the slippery, tenaciously adhering hydrogel coatings of the present invention. They also demonstrate the mechanical performance of coated devices, their wear resistance, and their resistance to the exertion of dynamic forces in blood. The examples also outline a suitable procedure for the measurement of both the dynamic behavior and permanence of the slippery, tenaciously adhering coatings of the present invention in blood.

Definitions

As used both in the examples and throughout the specification, the following designations, symbols, terms and abbreviations have the indicated meanings:

1. Molecular weights (MW) of polyols are number average molecular weights using the experimentally determined hydroxyl numbers of the polyols in accordance with ASTM D-4274-88, assuming that the functionality is known.
2. Equivalent Weights (EW) of polyols are number average equivalent weights of polyols as calculated on the basis of analytically determined hydroxyl numbers.
3. Isocyanate Equivalent Weights (EW/NCO) are number average equivalent weights of isocyanate prepolymers calculated on the basis of determination of % NCO of said prepolymers in accordance with ASTM D-4666-87 and/or equivalent test methods known in the art. For commercial monomeric diisocyanates, their derivatives, and HYPOL PreMA-G-50 prepolymer, published data exist.

4. "ml" denotes milliliters.

5. "Torr" denotes millimeters (mm) of mercury pressure [1 atmosphere=760 Torr (mm Hg)].

6. "ppm" denotes parts per million (catalyst concentrations, metals contents).

7. AMBERLYST 15 (ROHM & HAAS) denotes a strongly acidic macroreticular ion exchange resin, generally used for non-aqueous reactions.

8. AMBERLYST A-21 (ROHM & HAAS) denotes a weakly basic macroreticular ion exchange resin for removal of acidic anions from non-aqueous systems.

9. "Urethane-grade" denotes specially dried and/or distilled solvents used as diluents for the isocyanate prepolymer reactions and prepolymer coatings solutions of the present invention (driers normally comprise UOP molecular sieves, type 4A, or equivalent materials).

10. "Silicone" Coating comprises a 2% solution of DOW CORNING MDX4-4159 Fluid in n-heptane applied to the device. According to the DOW CORNING MSDS Data Sheet, MDX-4-4159 is a solution containing 34% Stoddard Solvent, 15% isopropyl alcohol, 1% dimethyl cyclosiloxanes, and 50% of dimethoxy silyl dimethyl aminoethyl amino propyl silicone polymer (all constituents are expressed in %, by weight).

11. "Ringer's Solution" is an isotonic saline solution comprising 0.86 gm of NaCl, 0.03 gm of KCl, and 0.033 gm of $CaCl_2$ in 100 ml of purified water.

12. "Footnotes 1 to 17" in Example 1, Table 1 describe the chemical nature of water-soluble polyether reactants and the polyisocyanates used for the preparation of the hydrophilic polyether prepolymers of the present invention.

13. HYPOL PreMa® G-50 comprises a hydrophilic polyether prepolymer based on IPDI (isophorone diisocyanate) available from HAMPSHIRE CHEMICAL CORP., Lexington, Mass., containing approximately 0.4 milliequivalent of NCO/gm.

14. A parison is a rod-like or tubular blank from which a balloon for a medical device is subsequently formed by blow-molding. Parisons are formed by direct extrusion of the plastic substrate material. Plastic parisons are useful as test substrates, and were used in the examples herein, because their geometric uniformity makes them easy to plasma-treat, and because they are readily adapted to drag force measurements.

15. The term hydrophilic refers to substances on which water droplets do not readily form beads on the surface of such substances, but, instead, the water droplets tend to assume a contact angle of less than 90° with the substance, and readily form a film on the surface of the substance. Hydrophilic substances may also tend to absorb water and swell to weights much greater than their dry weights.

EXAMPLES

Dynamic Drag Force Test Method

For the purpose of measuring drag forces on coated catheter tubes or balloon devices used in coronary angioplasty, it was necessary to develop an applicable test method which gave reliable comparisons with the prior art and between the different polymer compositions of the hydrophilic coatings of the present invention. Moreover, it was also decided to conduct the tests in different aqueous media, for example distilled water, saline solution (Ringer's Solution), blood plasma and in blood to investigate the influence of the most critical use environment the clinical devices can experience.

The test method for the measurement of friction and permanence for the antifriction coatings on plastic tubes of the present invention consisted of the following procedure:

Apparatus: INSTRON Tensile Tester, 20 lb load cell; test range 0–500 gm; cross head speed 20 inches/min up and down; 4 inch stroke, automatic cycle.

Test Fixture: Clamshell assembly with friction surface for holding coated plastic tube specimens. The friction surface was a commercial cleaning product SCRUNGE® available from Guardsman Products, Inc., Consumer Products Division, Grand Rapids, Mich. and sold in major food markets. The SCRUNGE® pad, consisting of ground rigid abrasive PU plastics particles surface-coated onto a flexible polyurethane foam matrix, was cut into 1×1.75 inch rectangles. The friction surfaces were moistened with the wetting fluid and folded in half with the abrasive surface inside. The tubular test specimen was enclosed in the folded friction surface and placed in the test fixture.

Test Parisons: The test parisons were thin wall plastic tubes, having a length of from about 6 inches to about 8 inches, an outside diameter (OD) of from 0.07–0.095 inch, and an inside diameter (ID) of from 0.04–0.07 inch. In the event the test sample was too flexible and buckled during the return cycle, a 0.066 inch OD braided wire rod was inserted into the test specimen (HYTREL and other relatively flexible tubing).

Wetting Medium: The wetting media tested were distilled water, Ringer's Solution, blood plasma, and defibrinated beef blood. The medium was delivered continuously to the tube at the top of the test fixture at the rate of 10 to 20 drops per minute, by means of capillary tubing using a syringe pump.

Test Procedure: A braided wire shaft was placed in a test sample, as necessary. The friction surface was wetted with appropriate test fluid. The friction surface was folded over the test sample, and the combination of the two was placed into the test fixture and the fixture was closed. The top end of the test sample was clamped into a clamp on the load cell. The INSTRON test machine was started, and drag force measurements were recorded at 1, 5, 10, 20, and 40 strokes.

Example 1

Rectification of Hydrophilic Polyether Precursors Based on Commercially Available Compounds for Use in Prepolymer Syntheses Initially the starting material selected for the evaluation of PU hydrogel materials to be affixed to ammonia plasma-treated surfaces consisted of HYPOL PreMa ®G-50, a commercially available PU hydrogel intermediate based on isophorone diisocyanate (IPDI) and a water soluble copolyether polyol. This prepolymer has a structure that appeared suitable for the preparation of the PU hydrogels of the present invention. Furthermore, it was represented to yield biocompatible polyurea polymers that appeared quite slippery. Consequently, this product was examined first in the attempt to perfect covalently-bonded hydrogels to ammonia plasma-treated substrates of interest for medical devices. However, it became soon apparent that this product contained very appreciable quantities of unreacted copolyether hydroxyls.

Commercially water-soluble homopolyethers and copolyethers containing from one to about three hydroxyl groups per macromolecule were selected as the first choice for starting materials for the synthesis of the prepolymers of the present invention. Most of these materials soon proved unsuitable because they contained sufficient quantities of alkali metals or alkali metal salts to interfere with the prepolymer reactions. Consequently, the products were ion-exchange treated by dissolving them at concentrations of about 50%, by weight, in solutions of isopropyl alcohol and stirring with excess quantities, in relation to estimated levels of metal catalyst impurities present, of about equal quantities of AMBERLYST 15 and AMBERLYST A-21 which had been preconditioned by immersion in isopropyl alcohol in order to remove the alkali metals and their salts. Some of the homopolyethers of ethylene oxide were solids at temperatures as high as 50° to 55° C. and in those cases, the isopropanol/polyether mixture was heated to about 60° C. and maintained there during the ion exchange reaction. In all other cases the ion-exchange treatment was conducted at from room temperature to about 40° C. Alternatively, the ion exchange refining is conducted in a continuous manner by means of mixed bed heated columns or separate columns using the cationic and anionic resins separately, as is well known in the art.

A slurry of the mixed ion exchange resins in the polyether/isopropanol dilution was agitated for a period of at least 6 hours. After that time, the resins were removed by filtration, and the ion exchange resins were washed with a portion of isopropyl alcohol to remove entrained polyether therefrom. For the homopolyethers from ethylene oxide, the rinse was conducted with preheated isopropanol (~60° C.). The rinse solutions were combined with the original filtrate for subsequent evaporation of the diluent and water present in the polyethers. Before handling the polyether materials at elevated temperatures in the presence of any air, they were protected by means of suitable antioxidants. For this purpose, a quantity of about 0.05%, by weight, based upon the original weight of polyether used for refining, of SANTONOX R (see also U.S. Pat. No. 4,886,866), was added and dissolved before subsequent solvent stripping operations.

The isopropyl alcohol was removed by distillation while blanketing the vessel with a slow stream of dry nitrogen to avoid contact with air. After distillation of the alcohol ceased, a small quantity of toluene or xylenes were added to the polyether residue and the materials were subjected to a gradually increasing vacuum. During this procedure, water and remaining traces of isopropanol were removed by means of azeotropic distillation. Finally, the polyether residue was subjected to a vacuum of from 5 to 1 torr at 100 to 120° C. for a period of 2 to 3 hours under a blanket of dry nitrogen. After this time, the polyether residue was allowed to cool to about 70° C., the vacuum was then discontinued while the vessel was brought to atmospheric pressure by means of blanketing with dry nitrogen. The polyether product was alternatively removed while still warm or was utilized directly for the prepolymer formation step. The polyether precursor was analyzed for hydroxyl number, % $H_2O$ (ASTM D4672-87) and ppm alkali metals, as necessary. To avoid complications due to side reactions from moisture, rehydration of the polyols was prevented by storing them under carefully monitored anhydrous conditions.

Example 2

Preparation of Cycloaliphatic Isocyanate Prepolymers from Commercially Available Ion-exchanged Polyether Precursors Because of the unsuitability of prepolymers prepared using the commercially available water-soluble homopolyethers and copolyethers of Example 1, it became necessary to explore the preparation and composition of a number of cycloaliphatic isocyanate prepolymers that appeared useful as starting materials for the PU hydrogels of the invention.

For the purpose of preparing the prepolymers designated A through P, presented in Table I, the polyether starting materials were heated to about 30° C. for materials which were liquid at room temperature, and to about 55° C. in the case of the solid homopolyethers, and the reactants were maintained throughout the procedure under a blanket of dry nitrogen. At this point the appropriate amount of catalyst, if any, was added to the reaction vessel. The calculated amount of diisocyanate was then added all at once, while the reactants were mixed thoroughly to effect immediate homogenous reaction conditions. The ensuing exotherm was moderated if necessary to attain a reaction temperature of 70° to 75° C. and the reactants were held at this temperature for a total of about 4 hours for the catalyzed reactions, and up to 24 hours for the non-catalyzed systems.

It was found that the reaction between the polyethers and the cycloaliphatic isocyanates DESMODUR W and IPDI were incomplete even after even 24 hours at the above reaction temperatures in the absence of catalyst. Consequently, the prepolymer synthesis procedure was eventually amended to use tin catalysts (dibutyltin dilaurate or stannous octoate) for all prepolymer syntheses with these relatively slow reacting diisocyanates. It was also discovered that it was easier to moderate the isocyanate reaction in the presence of aromatic hydrocarbons which were co-solvents for the polyethers and the cycloaliphatic isocyanates. The solvent which proved to be most useful was toluene, and the reactions were generally conducted as 50% dilutions between reactants and solvent, but it was also feasible to use 75% toluene and 25% reactants, if warranted. The solvent procedure also facilitated handling of the prepolymer materials for subsequent dilution with other solvents to the desired coatings compositions.

At the end of the prepolymer synthesis, the resulting products were analyzed for % NCO by the wet method with dibutylamine, a procedure well known in the art (ASTM D4666-87). For catalyzed reactions, the desired EW/NCO agreed quite well with the calculated values. In the case of uncatalyzed reactions, only the somewhat faster reacting aliphatic diisocyanates (HDI) gave acceptable results. Prepolymers containing polyethers having a propylene oxide content of at least about 15 to 20%, by weight, resulted in liquid polyether prepolymers that greatly facilitated handling of the coatings intermediates.

Table I, entitled "Composition of Hydrophilic PU Prepolymer Intermediates", lists the compositions, characteristics and preparation conditions of new intermediates A through P:

TABLE I

Composition of Hydrophilic PU Prepolymer intermediates

| RUN # | POLYETHER | STRUCTURE OXIDE/FUNCT. | MOL. WT. | ISO TYPE | OH TO NCO EQ RATIO[1] | CATALYST | PE/gm | ISO/gm | CAT/gm | PHYSICAL STATE ROOM TEMP |
|---|---|---|---|---|---|---|---|---|---|---|
| A | PEG 2,000[2] | EO - DI | 2,000 | W[3] | 2:3 | T-9[4] | 125.2 | 24.66 | 0.044 | Solid |
| B | PEG 3,400[5] | EO - DI | 3,400 | W | 2:3 | T-9 | 134.4 | 15.55 | 0.046 | Solid |
| C | PEG 8,000[6] | EO - DI | 8,000 | W | 1:2 | T-9 | 131.7 | 6.98 | 0.049 | Solid |
| D | PLURACOL V-10[7] | EO/PO - TRI | 22,000 | P | 1:2 | none | 64.8 | 1.82 | none | Liquid |
| E | PLURACOL V-10[9] | EO/PO - TRI | 22,000 | W | 1:2 | T-9 | 67.1 | 2.09 | 0.022 | Liquid |
| F | MPEG 5,000[10] | EO - MONO | 5,000 | I | 1:2 | none | 56.2 | 2.50 | none | Solid |
| G | MPEG 5,000 | EO - MONO | 5,000 | W | 1:2 | T-9 | 76.9 | 3.77 | 0.022 | Solid |
| H | UCON 75-H 90,000[11] | EO/PO - DI | 15,000 | I | 1:2 | none | 65.0 | 1.93 | none | Liquid |
| I | UCON 75-H 90,000 | EO/PO - DI | 15,000 | W | 1:2 | T-9 | 62.5 | 2.19 | 0.022 | Liquid |
| J | PEG 14,000[12] | EO - DI | 14,000 | I | 1:2 | none | 70.0 | 2.22 | none | Solid |
| K | PEG 14,000 | EO - DI | 14,000 | W | 1:2 | T-9 | 70.7 | 2.65 | 0.022 | Solid |
| L | UCON 75-H 9,500[13] | EO/PO - DI | 6,950 | I | 1:2 | none | 70.3 | 4.50 | 0.022 | Liquid |
| M | UCON 75-H-9,500 | EO/PO - DI | 6,950 | W | 1:2 | T-9 | 71.5 | 5.39 | none | Liquid |
| N | MPEG 5,000 | EO - MONO | 5,000 | I | 1:2 | T-12[14] | 56.2 | 2.50 | 0.00118 | Solid |
| O | UCON 75-H-90,000 | EO/PO - DI | 15,000 | W | 1:2 | T-12 | 62.5 | 2.19 | 0.00129 | Liquid |
| P | HCC G-50 EOPO[15] | EO/PO - TRI | ~7,300 | I | 1:2 | T-12 | 73.17 | 6.67 | 0.0016[16] | Liquid |
| Q | PreMA g-50[17] | EO/PO - TRI |  | I | 1:2.05 | none | — | — | none | Liquid |

[1]Reactant ratio - Equivalents of polyether hydroxyls to equivalents of NCO (ISO) compounds;
[2]Polyethylene glycol - MW~2,000;
[3]DESMODUR W, Cycloalipathic diisocyanate available from MILES CORP., Polymer Division; MW = 262.4, EW = 131.2;
[4]Stannous octoate; note: all uncatalyzed DESMODUR W systems tested contain free diisocyanate;
[5]Polyethylene glycol - MW~3,400;
[6]Polyethylene glycol - MW~8,000;
[7]Trifunctional copolyether polyol comprising trimethylolpropane adduct of 75/25 wt. % EO/PO - MW~7320, EW~131.2;
[8]Isophorone diisocyanate, available from HUELS AMERICA, Inc.; MW = 222.3, EW = 111.15;
[9]Trifunctional copolyether polyol comprising trimethylolpropane adduct of 75/25 wt. % Eo/PO - MW~22,000, EW~7330;
[10]Monofunctional methyl ether of polyethylene glycol - MW~5,000;
[11]Difunctional copolyether diol comprising 75/25 wt. % EO/PO - MW~15,000;
[12]Difunctional polyethylene glycol - MW~14,000;
[13]Difunctional copolyetherdiol - MW~6,950;
[14]Dibutyltin dilaurate; note: all uncatalyzed IPDI systems tested contain free diisocyanate;
[15]Precursor copolyether triol for HYPOL PreMA G-50 prepolymer (HAMPSHIRE CHEMICAL CORP.) believed to contain 75/25 wt. % of EO/PO; MW~7,300, OH No. = 23.0;
[16]Systems N, O and P were also run as 50% solutions in toluene for ease of handling and subsequent dilution to desired coatings concentrations and compositions;
[17]HYPOL PreMA G-50; non-catalyzed isophorene diisocyanate (IPDI) prepolymer from copolyether (15) and IPDI - EQ ratio 1:2.05; contains free IPDI and free hydroxyls.

Example 3

Processes for Plasma Treatment Intermediate Coating and Formation of Pu Hydrogels Plastic materials, having essentially no functional groups that were capable of reaction with the isocyanate group, were used to obtain covalent bonds with the hydrophilic hydrogel polymers of the present invention. Substrates such as PET, used in angioplasty balloons; HYTREL, used for catheter shafts; PE, used for various balloons; and hydrophobic nylon-11 and nylon-12 polymers, used in catheters and balloons, were considered as the most important thermoplastic polymer substrates for plasma treatment with nitrogen-containing gases to affix very reactive amino groups onto their surfaces. The formation of cohesive bonds with the substrate surfaces is often relatively difficult to accomplish, and it is not always easy to obtain good permanence even with polyurethane substrates. PET and HYTREL were utilized as the plastic substrates because they are typical surfaces that do not lend themselves to cohesive bonding unless the surfaces are either oxidized, treated with very aggressive solvents, or treated by other means. Test parisons of PET and HYTREL were therefore investigated very closely. It was the purpose of the experiment to prove that the affixation of amino groups upon the substrate surfaces would render them very reactive with the sluggish isocyanate groups of the hydrophillic isocyanate prepolymers of the present invention, which were preferable because of their greater biocompatibility over other more reactive PU hydrogel intermediates.

$NH_3$ was used as the plasma gas with the PLASMA SCIENCE PS 0350 Plasma Surface Treatment system, previously described in detail, and the experiment was conducted over a wide range of parameters. It was clearly established that for PET tubing (parisons having an OD of about 0.095 inches) use of $NH_3$ as the plasma gas resulted in improved adhesion of the PU hydrogel systems of the present invention, over an RF input range of from 20% power input (about 100 to 120 W) to 85% power input (about 450 to 470 W), at an ammonia gas flow rate of from about 50 std ml/min to about 730 std ml/min (the maximum flow rate attainable with the PS 0350 unit; higher flow rates may be attained using other apparatus), during exposure times of from about 30 seconds to about 3 minutes, and at a temperature in the range of from room temperature to about 40° C. Optimized results were observed and noted at about 100 W to about 400 W power input, and ammonia flow rates of from about 200 std ml/min to about 650 std ml/min. ESCA surface analysis indicated that best permanence was achieved at intermediate surface concentrations of amino groups on the PET surface. The usefulness of ammonia plasma treatment was also confirmed for parisons made from HYTREL. Due to the high elasticity of HYTREL, drag force measurements required the insertion of a braided guidewire in the inside lumen of the parison to obtain reliable INSTRON readings.

The influence of the ammonia plasma treatment was tested with "Silicone" coating on PET parisons in the presence of blood as the contact environment and compared with the PU/PUR hydrogel from HYPOL PreMA G-50, catalyzed versions thereof, as well as combination systems comprising PreMA G-50 and other PU/PUR hydrogel prepolymer coatings (see also Example 2 for synthesis of hydrophilic PU intermediates). The "Silicone" coating, was not helped by the $NH_3$ plasma treatment. Moreover, the "Silicone" coating did not show any kind of permanence in the presence of blood, the main body fluid tested. In contrast, the PU/PUR hydrogel coatings of the invention exhibited remarkably improved permanence in blood after ammonia plasma treatment. However, even the PU/PUR hydrogels without plasma treatment were also remarkably superior in this respect in relation to the "Silicone" coating.

Range finding tests with respect to concentration effects of the PU hydrogel intermediates (Example 2 and others) showed that suitable hydrogel coatings on the substrate surface are possible when the solids content of the coatings solution is within the range of from about 1.5% to about 6%, and when the dip time is from about 10 seconds to about 30 seconds. However, it is within the realm and scope of the invention to stay at the lower concentration range or even below, if the dipping time is extended, or relatively more aggressive solvents are used during the initial dipping procedure. Various known contacting methods, including spray coating, are also feasible. The insertion time of the device into the coating solution has a pronounced effect upon the quality of the coating. Other measures which influenced the coatings thickness and quality were the use of somewhat higher boiling solvents such as cellosolve acetate (UCC) and other similar slower evaporating materials as co-solvents with the lower boiling products such as MEK, ethers, and the like. Other materials which proved useful for the achievement of uniform coatings included minute quantities of surface active agents, for example, TERGITOL®X-100 (UCC) and thixotropic agents, such as amorphous silicas and other materials which are known to influence the quality and application of coatings to various substrates.

A double coating procedure using the same hydrophilic PU prepolymers or different prepolymers utilized in the present invention was also performed. HYPOL PreMA G-50 and Prepolymer P, double-coated with Prepolymer F or Prepolymer I and others (for compositions, see Table I of Example 2) gave even better results than the single coated versions of G-50 or P. The usefulness of such combinations was ascertained by testing various compositions in terms of the resulting drag force measurements and cycle testing for permanence of the coated parisons in blood after the completion of the hydrogel formation.

The formation of the polyurea (PUR) hydrogel was accomplished by means of exposing the coated device to atmospheric moisture or dip-coating the material in aqueous solutions of varying compositions. It was found useful to accelerate the PUR hydrogel formation by means of tertiary amine catalysts, reactive amine derivatives, or in the presence of mildly basic salts to speed up the hydrogel formation. The influence of moisture or the combination of the coating with aqueous amine solutions, for example ethylenediamine and other polyamines, results in the formation of polyurea hydrogels which form the focal point of the PU hydrogels of the present invention. Alternatively, the PUR hydrogel formation was performed at elevated temperatures, for example at temperatures up to 80° C., to speed up the cure times and make the process less time-dependent and more cost-effective. PUR hydrogel formation was also alternatively conducted in the presence of other compatible hydrophilic hydrogel polymers which are anchored to the substrate by means of the covalently bonded hydrophilic polyurethane-urea (PU/PUR) "tie-coat" of the invention. Still other process variations of the present invention may readily be apparent to one skilled in the art.

Example 4

Catalytic Synthesis of Hydrophilic Prepolymers

This example demonstrates the preparation of hydrophilic prepolymers prepared by the catalytic technique with 20 ppm of T-12 (dibutyltin dilaurate) catalyst as a 50% solution in toluene. In all cases the water-soluble polyether precursors were deionized by means of a slurry of AMBERLYST 15 and AMBERLYST A21 in isopropanol, and after filtration, the combined effluents were stabilized with 0.05%, by weight, of SANTONOX R. The isopropanol was then removed by distillation under atmospheric pressure until evolution ceased, and a small quantity of toluene was added and the distillation of toluene was continued to remove remaining isopropanol and moisture by azeotropic distillation while under a blanket of nitrogen throughout the refining cycle. The materials were then subjected to a vacuum of from about 5 Torr to about 10 Torr for a period of 3 hours at from about 100° C. to about 120° C. The polyether precursors were then charged to a prepolymer reaction flask, diluted with 50%, by weight, of toluene, and the required amount of T-12 catalyst, diluted in toluene, was added, while the reactants were kept under nitrogen at room temperature.

The proper amount of the diisocyanate, as a 50% solution in toluene, was then added all at once at room temperature and the exothermic adduct prepolymer formation was moderated as required to keep the reactants from exceeding 75° C. In the case of Prepolymer T, the initial toluene solution of the monofunctional EO homopolyether was held at from 45° to 50° C., to avoid crystalline deposition of the polyether. The reactants were agitated continuously under a stream of dry nitrogen and maintained at 70° to 75° C. for a period of 4 hours, and transferred into a dry nitrogen flushed container after this period of time. After at least 24 hours had elapsed, the NCO-terminated prepolymers were then analyzed for % NCO by the dibutylamine method. The following table shows reactant concentrations, % NCO content based on 100% solids, and calculated and theoretical values for % NCO. In all cases the diisocyanate charge represents 2 equivalents of NCO per equivalent of the hydroxyl polyether precursor.

TABLE 2

Charge Ratios and % NCO Contents for Prepolymers R, S and T

| Ingredients, gm | Prepolymer R | Prepolymer S | Prepolymer I |
|---|---|---|---|
| PLURACOL V-7 | 500.0 | 0 | 0 |
| UCON 75-H-90,000 | 0 | 500.0 | 0 |
| MPEG 5,000 | 0 | 0 | 500.0 |
| Toluene, total | 546.0 | 518.0 | 520.0 |
| IPDI | 45.6 | 0 | 22.2 |
| DESMODUR W | 0 | 17.5 | 0 |
| T-12 (~ 20 ppm) | 0.011 | 0.010 | 0.010 |
| Analysis % NCO | | | |
| Actual (100% solids) | 1.63 | 0.52 | 0.79 |
| Theoretical, calculated | 1.58 | 0.54 | 0.80 |

The above-described Prepolymers R, S and T correspond to catalyzed versions of P, O, and N (Table 1) and were prepared as 50% solutions in toluene. PLURACOL V-7 (BASF Corp.) is a trifunctional copolyether, which was used as the prepolymer precursor for R, is a 75/25%, by weight, random EO/PO polyether adduct of trimethylpropane having a OM No. of ≅23.0 and a calculated EW≅2340. The prepolymers were subsequently diluted further to about 25% of solids with more toluene and an aliquot thereof was stored at 20° C. to 25° C. for a period of 4 months. The prepolymers remained stable over this period of time and showed no evidence of gelation, indicating an extended shelf stability despite the presence of tin catalyst. Prepolymer T crystallized at ambient temperature, but could be melted readily by heating the solid to 45 to 50° C. For coating of catheters, balloons and other medical devices, the toluene solutions of the hydrophilic prepolymers were further diluted in suitable co-solvents, to a solids content of, for example, 2% by weight, before proceeding to the coating step, According to the % NCO analysis recorded for the above prepolymers, the isocyanate reaction proceeded to completion when catalyzed even at very low tin catalyst levels which were found not to impair biocompatibility for the catheter devices.

Example 5

Evaluation of PU Hydrogels

For the purpose of evaluating the PU hydrogel coatings of the present invention, from which the exhibition of superior lubricity, wear performance and durability when contacted with body fluids, is required, it was decided to deposit the coatings on plasma-treated plastic substrates that were known to have only a limited capability to result in durable covalent bond fixation in the absence of pretreatments. Typical application in the medical devices field comprise the low friction coatings of catheter balloons and other catheter components which are used in coronary angioplasty, where the devices must not only resist excessive wear and maintain permanence during transfer through blocked blood vessels but must also exhibit excellent lubricity while traversing obstructions, and often demand complex handling during manipulations of the device during clinical use. Consequently, initial coating tests were undertaken with PET and HYTREL substrates which are often used as materials of construction for such devices, or portions thereof. For that purpose, it was decided to utilize test parisons of ammonia plasma-treated PET tubing having dimensions of approximately 6 to 8 inch length, 0.07 to 0.095 inch OD, and 0.04 to 0.07 inch ID. For the evaluation of many characteristic PU hydrogel coatings of the present invention, samples having various compositions as described in Examples 3 and 4 above were utilized. PET parisons were treated with $NH_3$ plasma under conditions described in Example 3.

For the establishment of suitable comparison drag force testing, the plasma treatment for this particular analysis protocol was kept constant and included exposing the parisons in the HIMONT Plasma Science 0350 Unit to an initial vacuum of 0.01 torr followed by application of the ammonia gas plasma at a gas flow rate of 600 ml/min, at a power input of 120 watts and a frequency of 13.56 MHz, at a temperature of from 25° to 40° C., for a period of 3 minutes. The plasma-treated parisons were used within a period of from one to three weeks to eliminate anomaly due to possible fading of the plasma treatment with extended age. The hydrophilic PU prepolymers were diluted with MEK to a solids content of 2%, by weight, and the parisons were dip-coated by insertion therein for a period of 30 seconds, and allowed to dry in a forced air hood at room temperature.

In the case of the double coating procedure, the second coat was applied 60 minutes after the first coat had been affixed and then allowed to dry again in the hood. The coatings were then exposed to a minimum of 50% relative humidity for 72 hours, before being tested in the INSTRON drag force testing fixture described previously. The drag forces (gm) were recorded after 1, 5, 20 and 40 strokes in defibrinated bovine blood as the contact media. It had previously been determined that blood is much more aggressive than saline solutions, or water, both of which have heretofore been traditionally employed for performance and durability testing in the catheter art. The results of Table 3 represent averages of at least 4 specimen tested in defibrinated bovine blood.

TABLE 3

Drag Forces Tests of PU Coated Ammonia Plasma-Treated PET
DRAG FORCE in gm at NUMBER OF CYCLES (1, 5, 20, and 40)

| SAMPLE TYPE | STROKE -1 | STROKES -5 | STROKES -20 | STROKES -40 |
|---|---|---|---|---|
| SILICONE | 40 | 165 | 225 | >300 |
| HYPOL PreMA ® G-50 | 85 | 90 | 90 | 120 |
| A | 112 | 185 | 202 | 203 |
| B | 101 | 167 | 208 | 198 |
| C | 65 | 73 | 92 | 110 |
| D | 170 | 150 | 150 | 150 |
| E | 98 | 132 | 152 | 164 |
| F | 80 | 110 | 110 | 110 |
| G | 112 | 130 | 130 | 130 |
| H | 90 | 130 | 130 | 130 |
| I | 40 | 60 | 75 | 85 |
| J | 150 | 200 | 225 | 300 |
| K | 42 | 80 | 95 | 110 |
| L | 50 | 80 | 85 | 90 |
| M | 70 | 90 | 110 | 130 |
| N | 80 | 115 | 118 | 120 |
| 0 | 45 | 55 | 80 | 90 |
| P | 75 | 90 | 95 | 115 |
| R | 80 | 92 | 97 | 110 |
| S | 85 | 100 | 125 | 135 |

Note:
Specimens showing drag forces of >300 gm in blood bind in fixture during test.

Similar experiments were run in a few instances with plasma-treated coatings deposited on parisons made from HYTREL® and in general similar results were observed. The experiments show that the "Silicone" coating gives very good results upon starting of the initial tests, but loses its lubricity very quickly when exposed to blood as the contact medium. The PU hydrogels prepared in accordance with the present invention showed particularly good permanence and lubricity in the presence of blood as the medium. These phenomena, however, are unexpected and are not predictable based on the feel of the coatings when touched, since the "Silicone" coating feels very "slippery" when first touched, but loses its efficacy completely during the test in bovine blood. The hydrogel polymers of the present invention have good permanence characteristics apparently because of the excellent bonding with the ammonia plasma-treated PET and HYTREL substrates. Preliminary experiments with other ammonia plasma-treated substrates such as TPU, nylons and PE suggest the obtention of similar results.

Example 6

Drag Force Determination

This example presents data for the drag force determination of double-coated PU hydrogel systems with HYPOL PreMA G-50 and related hydrophilic prepolymers as the base coats, and various other hydrophilic prepolymers as the second coat, followed by transformation of both coats to the highly hydrophilic PU hydrogel in the presence of atmospheric moisture at a relative humidity of at least about 50%. Test specimens were ammonia plasma-treated PET parisons made in accordance with the conditions described in Example 4. Both coats involved the use of prepolymer dilutions to 2% by weight, with MEK, and the parisons were immersed into the first coatings solution for a period of about 30 seconds, allowed to dry for about 30 minutes at room temperature in a forced air hood, whereupon the second coat was applied and allowed to dry in the same manner.

The preparation of the hydrogel was conducted by exposing the coated parisons to an atmosphere of at least 50% relative humidity for a period of 72 hours, at room temperature, and then post-curing in a vacuum oven, maintained at a temperature of from about 60° C. to about 70° C., for a period of from about 1 to 2 hours, followed by measurement of the drag force as described above. Table 4 illustrates the drag force test results of ammonia plasma-treated double-coated PET parisons and specifies the prepolymer coatings systems. The numbers are averages of four determinations for each coating composition.

TABLE 4

Drag Force Tests of Double-Coated PET Parisons
DRAG FORCE in gm at NUMBER OF CYCLES (1, 5, 20, and 40)

| SAMPLE TYPE | STROKE -1 | STROKES -5 | STROKES -20 | STROKES -40 |
|---|---|---|---|---|
| PreMA ® G-50 | 85 | 90 | 100 | 120 |
| G-50 + B | 121 | 192 | 225 | 235 |
| G-50 + C | 53 | 60 | 66 | 79 |
| G-50 + D | 70 | 86 | 98 | 97 |
| G-50 + E | 50 | 88 | 118 | 148 |
| G-50 + F | 40 | 40 | 40 | 40 |
| G-50 + G | 108 | 152 | 168 | 175 |
| G-50 + H | 83 | 200 | 235 | 255 |
| G-50 + I | 35 | 60 | 75 | 86 |
| G-50 + J | 85 | 110 | 122 | 150 |
| G-50 + K | 100 | 148 | 155 | 190 |
| G-50 + L | 30 | 80 | 85 | 90 |
| R + T | 50 | 60 | 85 | 90 |
| S + T | 60 | 72 | 87 | 115 |

The combination of two coats of the hydrogels of the present invention exhibited synergistic effects with respect to the quality of the coatings. In particular it was surprising that the monofunctional isocyanate adduct shown as compounds F and T (precursor monofunctional homopolyether of EO having a MW of ~5,000) appeared particularly effective as a second coat. This material may act as a chain-stopper for the hydrogel polymer. Difunctional isocyanate adducts also gave improved results. Of particular importance is the efficacy of the second coat with respect to durability and good lubricity of the hydrogel coating in blood over an extended cycle of up to 40 strokes, representing a significantly longer duration.

Example 7

Comparative Test of Inventive and Prior Art Coatings in Several Media

Very surprisingly, the hydrophilic hydrogels affixed to plasma-treated surfaces according to the present invention showed no unusual results when tested in media typically utilized by others to test the properties of low friction coatings. Previous commercial materials had usually been tested in water, or Ringer's Solution. The efficacy of the covalently bonded PU/PUR hydrogel coatings was comparatively tested in the presence of water, Ringer's solution and blood media. Dynamic testing of the PET and HYTREL® parisons was conducted in the presence of bovine blood to determine whether there existed unusual interactions between commercially available coatings and the coatings of the present invention in the presence of blood as the test media. This was done in view of observations by others that the lubricity of many coated catheters of the prior art lacked permanence.

The results are presented in Table 5:

TABLE 5

Comparison Drag Force Tests In Various Media
DRAG FORCE in gm at NUMBER OF CYCLES (1, 5, 20, 40)

| PET PARISON TEST MEDIUM | STROKE -1 | STROKES -5 | STROKES -20 | STROKES -40 |
|---|---|---|---|---|
| UNCOATED PET | | | | |
| Water | 142 | 150 | 160 | 160 |
| Ringer's Solution | 70 | 75 | 75 | 75 |
| Blood | 230 | 220 | 220 | 220 |
| UNTREATED PET "Silicone" Coating | | | | |
| Water | 45 | 40 | 44 | 45 |
| Ringer's Solution | 59 | 59 | 60 | 60 |
| Blood | 45 | 165 | 225 | >300 |
| PLASMA-TREATED PET HYPOL PreMA ® G-50 | | | | |
| Water | 100 | 100 | 100 | 100 |
| Ringer's Solution | 54 | 54 | 67 | 75 |
| Blood | 77 | 79 | 91 | 105 |
| "Silicone" Coating | | | | |
| Water | 35 | 40 | 43 | 45 |
| Ringer's Solution | 55 | 55 | 55 | 60 |
| Blood | 35 | 155 | 230 | >300 |

Note:
Specimens showing drag forces of >300 gm in blood bind in fixture during testing.

The above comparative tests illustrate that the uncoated PET parisons when tested in the test fixture previously described herein exhibited relatively high drag forces in water, low drag forces in Ringer's isotonic saline solution, and consistently high drag forces in blood. The "Silicone" coating gave low drag forces in both water and saline solution even after 40 strokes, but was not at all effective in blood. This tends to confirm clinical experience.

HYPOL PreMA® G-50, a typical PU/PUR hydrogel of the present invention, gave good results in Ringer's solution and moderately acceptable results in water. However, the efficacy of the PU hydrogels in blood was clearly demonstrated. All PU/PUR hydrogel polymer intermediates synthesized were investigated in blood to verify the surprising lubricity and permanence of such coatings when deposited upon substrates that cannot react readily with isocyanates or form physical (noncovalent) bonds with the relatively slow reacting biocompatible hydrophilic PU intermediates of the present invention. Similarly excellent results were obtained with the PU hydrogel coatings of the present invention when deposited on nitrogen-containing plasma-treated substrates of thermoplastic PU, nylon, HYTREL, and dual oxygen- and nitrogen- gas plasma-treated PE polymer substrates, or alternatively, oxygen or air plasma-treated, or oxygen or air plasma-treated polymer substrates in the presence of argon (Ar) gas followed by fairly rapid treatment with a stream of gaseous ammonia without plasma.

Example 8

Radiation Exposure of Coatings

The behavior of the PU/PUR hydrogel coatings of the present invention when exposed to γ-radiation, as is used to sterilize medical devices prior to clinical use, was evaluated. For this purpose a limited number of ammonia plasma-treated PET parisons that were coated with several representative PU/PUR hydrogels were tested under dynamic conditions in blood before and after exposure to γ-radiation. The radiation dosage was selected upon the basis of previous experience with respect to sterilization of medical devices. Table 6 shows clearly that radiation does not interfere with the performance of the low friction coatings of the present invention when immersed in blood:

TABLE 6

Effect of Gamma Radiation on Performance of Coatings
DRAG FORCE in gm at NUMBER OF CYCLES (1, 5, 20, 40)

| PLASMA-TREATED PET RADIATION TREATMENT | STROKE -1 | STROKES -5 | STROKES -20 | STROKES -40 |
|---|---|---|---|---|
| BEFORE GAMMA | | | | |
| HYPOL PreMa ® G-50 | 62 | 73 | 85 | 107 |
| G-50 + C | 75 | 84 | 110 | 120 |
| G-50 + E | 55 | 86 | 100 | 105 |
| Prepolymer C | 66 | 102 | 108 | 112 |
| Prepolymer E | 64 | 96 | 107 | 117 |
| AFTER GAMMA | | | | |
| HYPOL PreMa ® G-50 | 44 | 66 | 108 | 140 |
| G-50 + C | 40 | 76 | 104 | 110 |
| G-50 + E | 60 | 104 | 104 | 120 |
| Prepolymer C | 100 | 120 | 130 | 130 |
| Prepolymer E | 52 | 102 | 109 | 111 |

Note:
Samples from 2% solution; Radiation; 2.5 to 3.8 megarads; Test Medium: Blood Example 9

Reactivation of Coatings

After the preparation of the final hydrogel which is covalently bonded to the nitrogen containing plasma-treated substrate, or to an aminosilane coated metal part, medical devices coated with coatings of the present invention are preferably dried, packaged in materials which are not moisture-permeable, and sterilized before use under clinical conditions. Drying of the device requires complete evaporation of the water from the hydrogel barrier coating. Because the dry hydrophilic PU/PUR base hydrogel is elastomeric, the coating does not flake or crack during drying. This can be accomplished by vacuum-drying of the apparatus under conditions well known in the art. For the purpose of examining rehydration, the coated parisons were vacuum-dried under standard conditions, heat-sealed inside a polyethylene film of suitable thickness and then exposed to γ-radiation to sterilize the specimens. After a period of 2 weeks the dry parisons were exposed to moisture by insertion into Ringer's solution or distilled water. The hydrogel test specimens appeared rehydrated within 10 to 15 seconds, or less. Upon subsequent measurement of the dynamic drag force in blood, excellent low force readings were observed and the coatings were as wear-resistant as freshly prepared materials.

What is claimed is:

1. A medical device comprising a polymeric or metallic substrate coated with a sterilized coating prepared by a process comprising:

a) making at least a portion of an outer surface of said polymeric or metallic substrate from which said medical device is fabricated, chemically reactive by affixing reactive chemical functional groups thereto;

b) coating the resulting reactive outer surface of said substrate with a first coating comprising a hydrophilic prepolymer intermediate, which is capable of forming a polyurethane-polyurea hydrogel-forming polymer, and which contains terminal isocyanate groups, such that at least a portion of said terminal isocyanate groups are reacted with and are covalently bonded to said reactive chemical functional groups on said surface of said substrate, forming covalent polyurea bonds therewith, resulting in the formation of a tie coat of a polyurethane-polyurea hydrogel-forming polymer, that adheres to said reactive outer surface of said substrate, and wherein at least a portion of said terminal isocyanate groups of said polyurethane-urea prepolymer intermediate are present in said polyurethane-polyurea hydrogel-forming polymer, such that they remain free to react with other species;

c) coating said tie coat with a second coating comprising a moisture-containing hydrogel-forming compound, further containing isocyanate-reactive chemical functional groups, such that a barrier coat of a hydrogel is formed upon the application of said second coating to said tie coat of said first coated substrate;

wherein said isocyanate-reactive functional groups of said moisture-containing hydrogel-forming compound are reacted with and are covalently bonded to at least a portion of said terminal isocyanate groups of said polyurethane-polyurea hydrogel-forming polymer that remain free to react with other species, to form a polyurethane-polyurea polymer hydrogel, that is adhering to said substrate surface;

d) drying said polyurethane-polyurea polymer hydrogel coating formed in step (c) to form a dried hydrogel coating thereof, and e) sterilizing the resulting coated medical device, bearing said dried hydrogel coating of step (d).

* * * * *

UNITED STATES PATENT AND TRADEMARK OFFICE
CERTIFICATE OF CORRECTION

PATENT NO.   : 6,265,016 B1
DATED        : July 24, 2001
INVENTOR(S)  : Fritz Hostettler et al.

It is certified that error appears in the above-identified patent and that said Letters Patent is hereby corrected as shown below:

Column 15,
Line 66, delete "pentaerythrtol," insert -- pentaerythritol --.

Column 18,
Line 15, delete "desiccants," insert -- diisocyantes --.

Column 19,
Line 19, delete "Modem," insert -- Modern --.

Column 32,
Line 36, delete "C.in," insert -- C. In --.

Signed and Sealed this

Fourth Day of June, 2002

Attest:

JAMES E. ROGAN
Attesting Officer
Director of the United States Patent and Trademark Office